US012415864B2

(12) United States Patent
Danielczyk et al.

(10) Patent No.: US 12,415,864 B2
(45) Date of Patent: Sep. 16, 2025

(54) HUMANIZED ANTIBODIES AGAINST LEWIS Y

(71) Applicant: Pentixapharm AG, Würzburg (DE)

(72) Inventors: Antje Danielczyk, Berlin (DE); Johanna Gellert, Berlin (DE); Anke Flechner, Berlin (DE); Patrik Kehler, Berlin (DE)

(73) Assignee: Pentixapharm AG, Würzburg (DE)

(*) Notice: Subject to any disclaimer, the term of this patent is extended or adjusted under 35 U.S.C. 154(b) by 525 days.

(21) Appl. No.: 18/010,858

(22) PCT Filed: Jun. 29, 2021

(86) PCT No.: PCT/EP2021/067767
§ 371 (c)(1),
(2) Date: Dec. 16, 2022

(87) PCT Pub. No.: WO2022/002887
PCT Pub. Date: Jan. 6, 2022

(65) Prior Publication Data
US 2023/0235076 A1 Jul. 27, 2023

(30) Foreign Application Priority Data
Jun. 30, 2020 (EP) .................... 20183237

(51) Int. Cl.
C07K 16/28 (2006.01)
A61K 47/68 (2017.01)
A61P 35/00 (2006.01)

(52) U.S. Cl.
CPC ...... *C07K 16/2896* (2013.01); *A61K 47/6817* (2017.08); *A61K 47/6849* (2017.08); *A61P 35/00* (2018.01); *C07K 2317/24* (2013.01); *C07K 2317/33* (2013.01);
(Continued)

(58) Field of Classification Search
None
See application file for complete search history.

(56) References Cited

U.S. PATENT DOCUMENTS 5,874,060 A 2/1999 Armour et al.
2008/0268459 A1 10/2008 Liu et al.

FOREIGN PATENT DOCUMENTS

AT 413487 B 3/2006
CN 102753199 A 10/2012
CN 113214402 A 8/2021
(Continued)

OTHER PUBLICATIONS

Rosok, M.-J., et al., "A Combinatorial Library Strategy for the Rapid Humanization of Anticarcinoma BR96 Fab," The Journal of Biological Chemistry, vol. 271 (37): Issue of Sep. 13: 22611-22618 (1996).
(Continued)

*Primary Examiner* — Karl J Puttlitz
(74) *Attorney, Agent, or Firm* — Nelson Mullins Riley & Scarborough LLP; Jane E. Remillard, Esq.; Jill Gorny Sloper, Esq.

(57) ABSTRACT

The present invention pertains to humanized anti-Lewis Y antibodies which specifically bind to Lewis Y and do not show any cross-reactivity. Especially, the humanized anti-Lewis Y antibodies do not bind to Lewis b or any other blood group carbohydrate antigen. In particular, the present invention is directed to humanized anti-Lewis Y antibodies which are useful in the treatment of cancer.

18 Claims, 13 Drawing Sheets

Specification includes a Sequence Listing.

(52) U.S. Cl.
CPC .... *C07K 2317/52* (2013.01); *C07K 2317/565* (2013.01); *C07K 2317/73* (2013.01); *C07K 2317/92* (2013.01)

(56) References Cited

FOREIGN PATENT DOCUMENTS

| WO | 2002/092126 A1 | 11/2002 |
| WO | 2008/028686 A2 | 3/2008 |
| WO | 2021019095 A1 | 2/2021 |

OTHER PUBLICATIONS

Yongqiang, W. et al., "Research progress on humanized monoclonal antibody," Prog in Microbiol Immunol Nov., vol. 36 (2): 6 pages (2008).

Brodin T. et al., "A Monoclonal Antibody That Recognizes Both LEB adn Y (LEY) Antigens," Glycoconjugate, vol. 4 (4):399-406 (1987).

Christensen P.A .et al., "Modifying Antibody specificity by chain shuffling of VH/ VL between antibodies with related specificities," Scandinavian Journal of Immunology, vol. 69(1): 1-10 (2009).

Christensen P.A., "The Lewis Y Antigen:Recognition and Mimicry," pp. 1-112, XP055843771, (2015) Berlin Retrieved from the Internet: URL:https://refubium.fu-berlin.de/handle/fub 188/5490 [retrieved on Sep. 22, 2021].

International Search Report and Written Opinion, PCT/EP2021/067767, dated Sep. 6, 2021, 12 pages.

Noble, P. et al., "Therapeutic Targeting of Lewis y and Lewis b with a Novel Monoclonal Antibody 692/29," PLOS , vol. 8(2): e54892: 12 pages (2013).

Westwood, J. et al. "Adoptive transfer of T cells modified with a humanized chimeric receptor gene inhibits growth of Lewis-Y-expressing tumors in mice," PNAS, vol. 102(52) 19051-19056 (2005).

Figure 2:
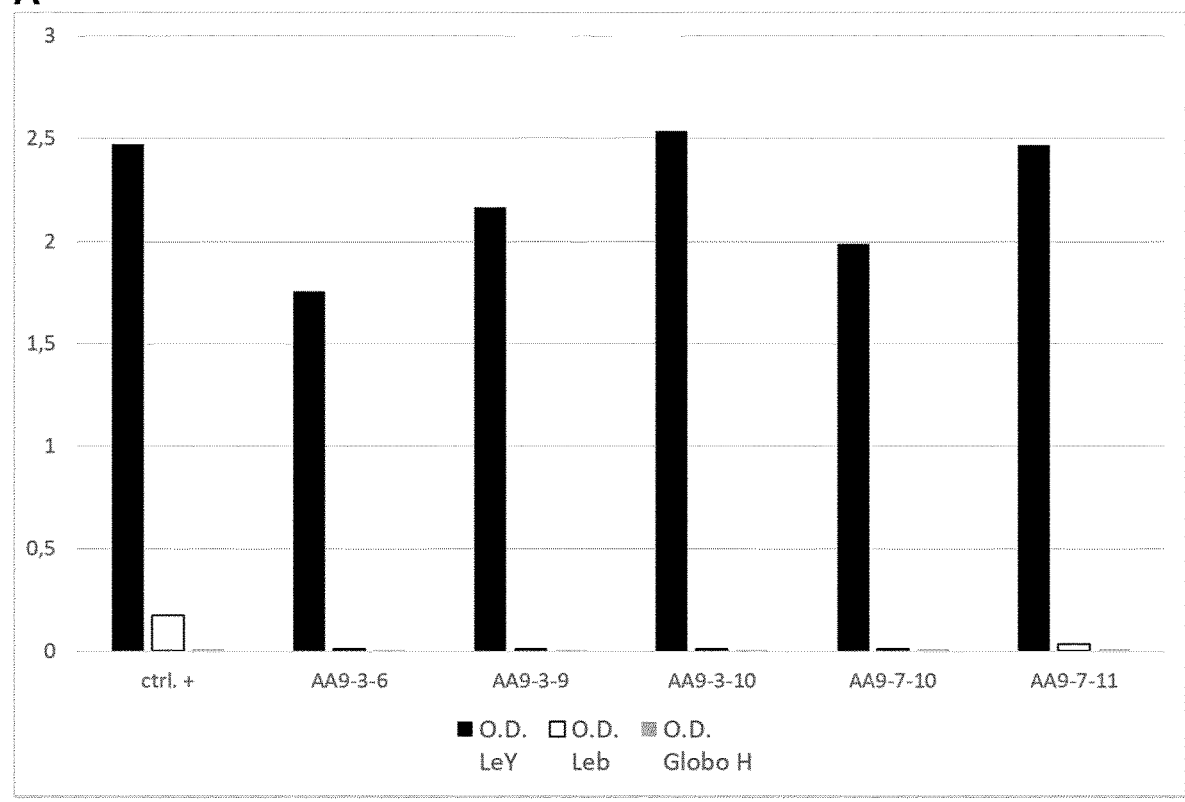
Figure 2:
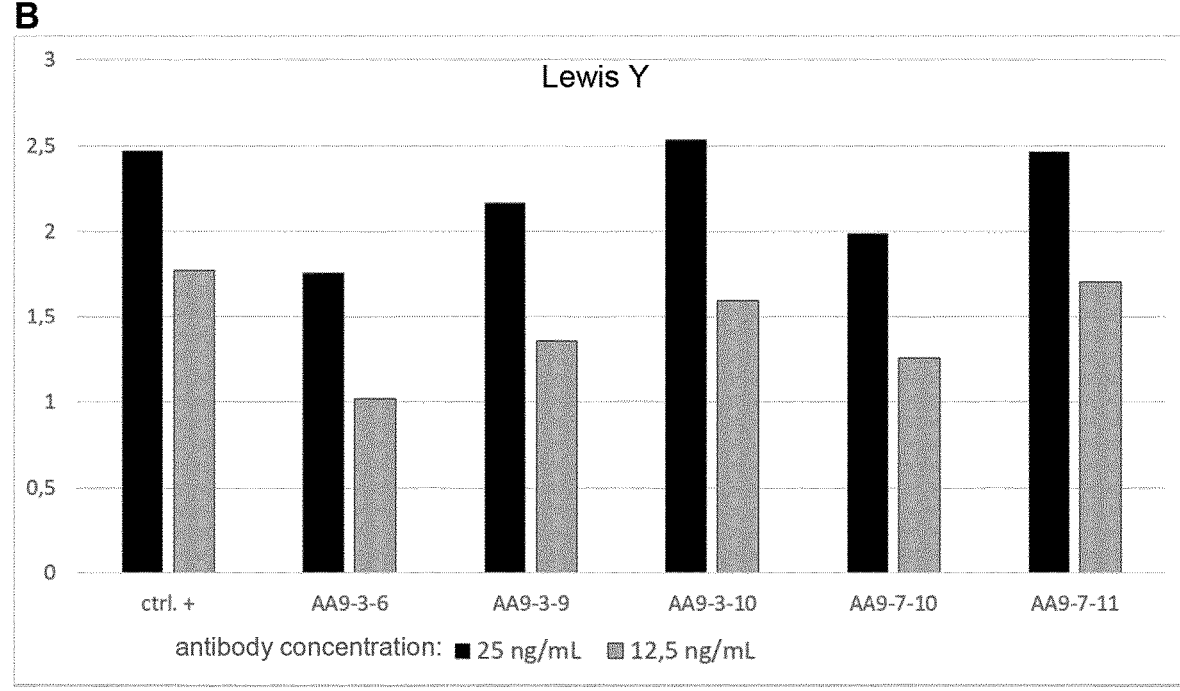

Figure 2 - continued
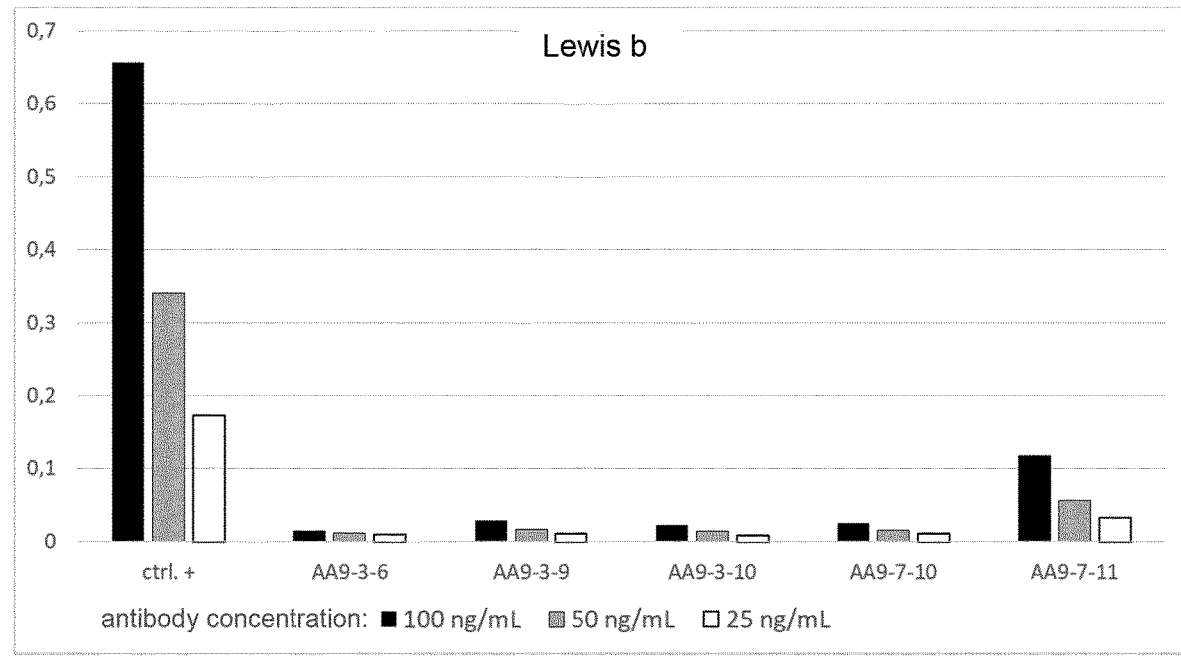
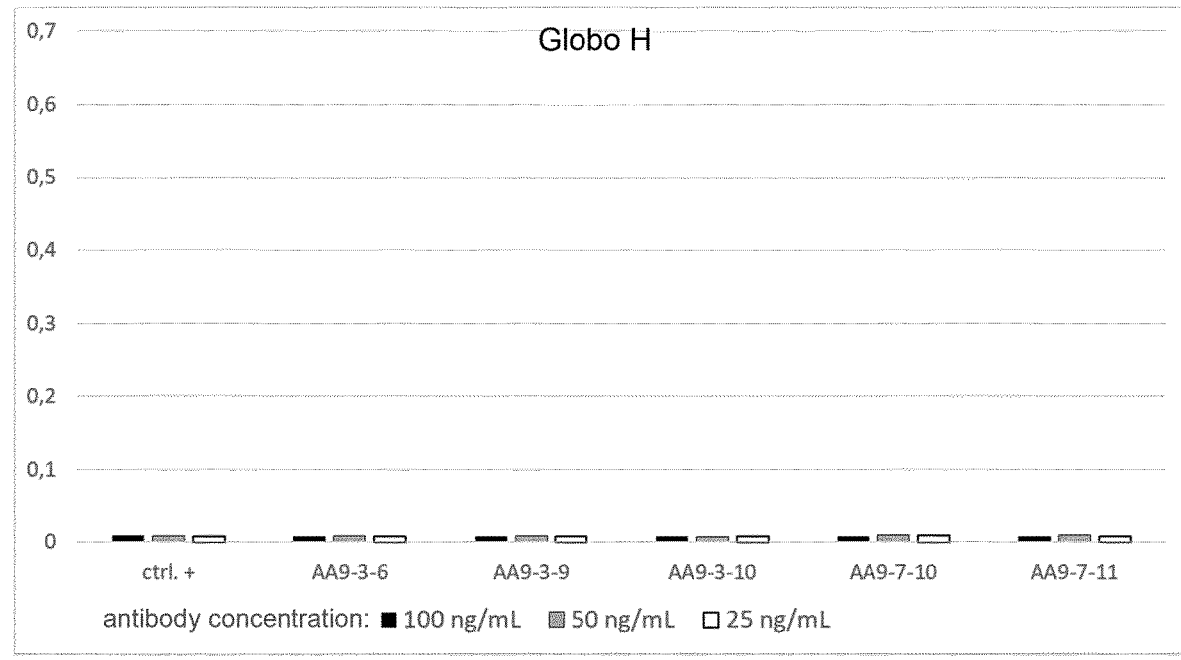

A

B

Figure 6:
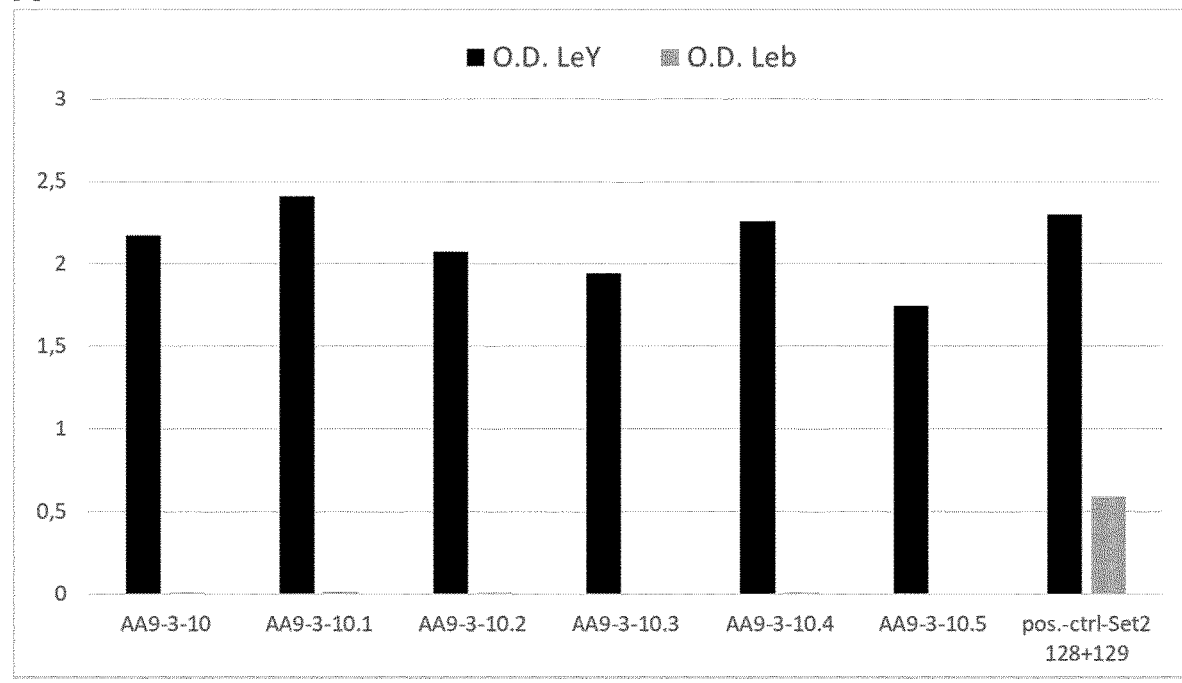
Figure 6:
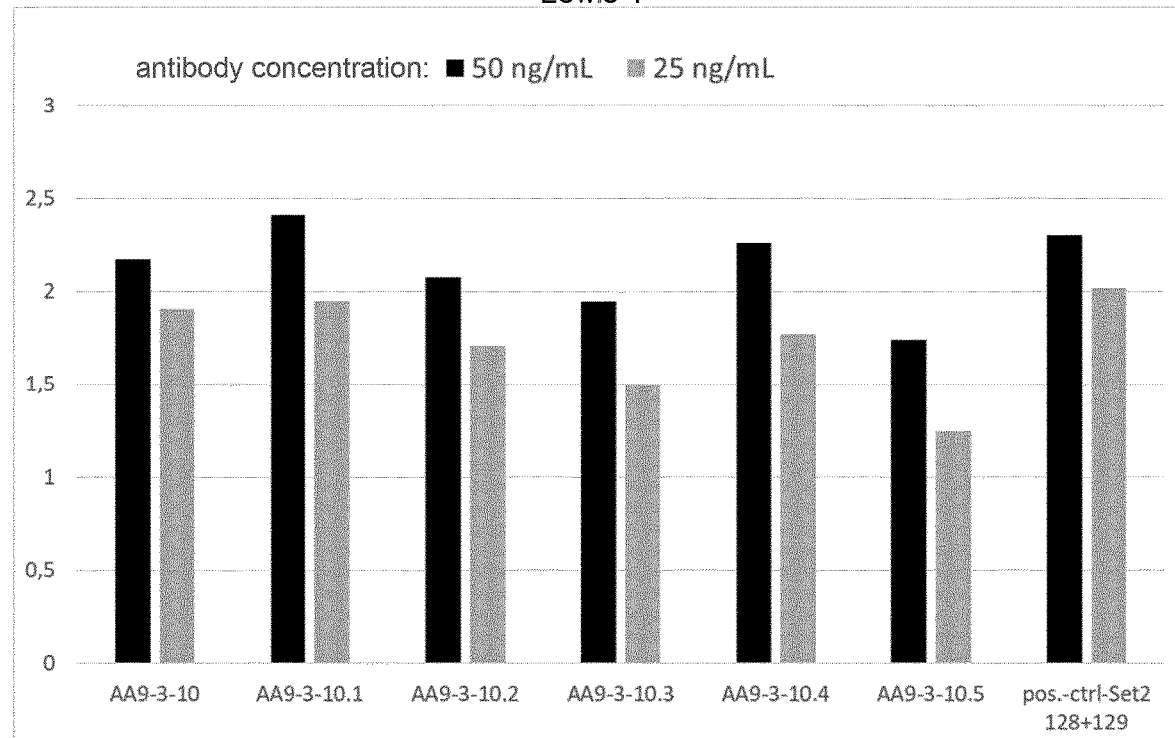

Figure 6 – continued
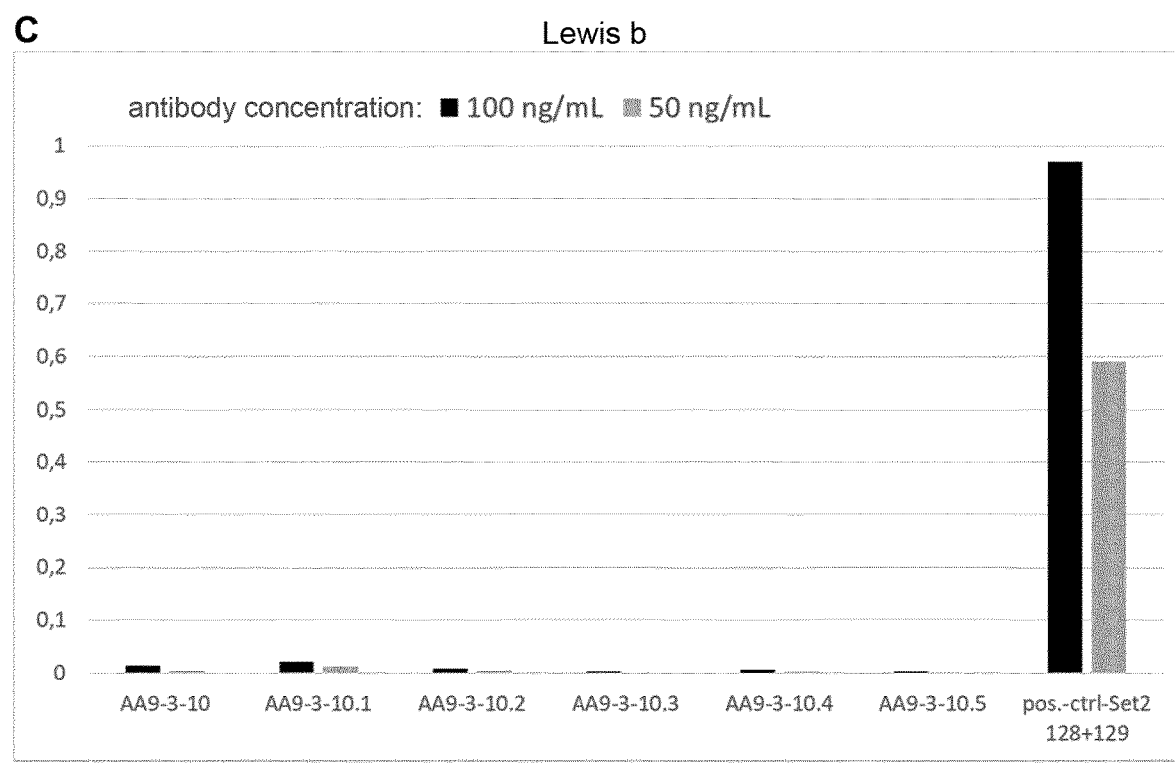

HUMANIZED ANTIBODIES AGAINST LEWIS Y

CROSS-REFERENCE TO RELATED APPLICATIONS

This application is a 35 U.S.C. § 371 national stage filing of International Application No. PCT/EP2021/067767, filed on Jun. 29, 2021, which claims the benefit of European Patent Application No. 20183237.5, filed on Jun. 30, 2020. The entire contents of each of these applications are incorporated herein by reference in their entirety.

SEQUENCE LISTING

The instant application contains a Sequence Listing which has been submitted electronically in ASCII format via EFS-Web and is hereby incorporated by reference in its entirety. Said ASCII copy, created on Dec. 16, 2022, is named KNJ-060US_Sequence-Listing.txt and is 27510 bytes in size.

FIELD OF THE INVENTION

The present invention pertains to the field of antibodies. In particular, a humanized anti-Lewis Y antibody showing exceptional target specificity and affinity for the glycan antigen is provided. In specific embodiments, the present invention is directed to humanized anti-Lewis Y antibodies for therapeutic and diagnostic use.

BACKGROUND OF THE INVENTION

Today, antibodies are widely used agents in the field of medicine and research. In medicine, they find application in many different fields. For example, antibodies are used as therapeutic agents in the treatment and prophylaxis of a variety of diseases such as cancer, cardiovascular diseases, inflammatory diseases, macular degeneration, transplant rejection, multiple sclerosis, and viral infections. In these therapies, the antibody may possess therapeutic activity on its own, for example by blocking receptors or messenger molecules, thereby inhibiting their disease-relevant functions, or by recruiting and activating components of the patient's immune system.

Specific antibodies are produced by injecting an antigen into a mammal, such as a mouse, rat, rabbit, goat, sheep, or horse. Blood isolated from these animals contains polyclonal antibodies directed against said antigen in the serum. To obtain an antibody that is specific for a single epitope of an antigen, antibody-secreting lymphocytes are isolated from the animal and immortalized by fusing them with a cancer cell line, resulting in hybridoma cells. Single hybridoma cells are then isolated by dilution cloning to generate cell clones that all produce the same monoclonal antibody.

However, in therapeutic applications these monoclonal antibodies have the problem that they are derived from animal organisms and differ in their amino acid sequence from human antibodies. The human immune system hence recognizes these animal antibodies as foreign and rapidly removes them from circulation. Furthermore, systemic inflammatory effects may be caused. A solution to this problem is the replacement of certain constant parts of the monoclonal antibody with corresponding parts of a human antibody. If only the heavy and light chain constant regions are replaced, a chimeric antibody is obtained, while the additional replacement of the framework regions of the heavy and light chain variable regions results in so called humanized antibodies.

In research, purified antibodies are used in many applications. They are most commonly used to identify and locate biological molecules such as in particular proteins. The biological molecules may either be detected after they have been isolated, for example to determine their presence, concentration, integrity or size. On the other hand, they may be detected in cellular or tissue samples, for example to determine their presence or location. Furthermore, antibodies are used in isolation procedures of specific biological substances, in particular proteins, wherein the antibody specifically separates the biological substance of interest from the sample containing it.

In all these applications, a tight binding and specific recognition of the antigen is of vital importance for the antibody used. Thereby, higher activity and less cross-reactivity, in particular less adverse side effects in therapeutic applications, are obtained. However, during humanization of monoclonal antibodies, often the affinity and specificity of the engineered antibody is decreased.

An interesting and important group of antibodies are those directed against carbohydrate moieties. Especially histo-blood group carbohydrate chains are interesting targets for antibodies since they are often tumor-specific or tumor-associated antigens. For example, cells of several different epithelial cancers, including breast, bladder, colon, stomach, pancreas, prostate, ovarian and small-cell lung cancer, expressed the carbohydrate structures Lewis Y [Fucα1-2Galβ1-4(Fucα1-3)GlcNAcβ-], also called LeY, more abundantly than any cell surface protein antigen. In the respective tumors, a high percentage of tumor cells is LeY positive, including even cancer stem cells. These carbohydrate antigens are therefore potential targets for tumor imaging, and active or passive immunotherapy.

Antibodies against these carbohydrate structures are often associated with several problems. Especially, unwanted side effects may occur due to the presence of identical or closely related carbohydrate structures found on normal tissues such as H type 2 expression on erythrocytes, or Lewis X on human myeloid cells, e.g. mature granulocytes. For example, several antibodies against LeY failed in clinical trials because they were cross-reactive to LeX and showed unfavorable efficacy and/or safety profiles. In addition, cross-reactivities to other glycan epitopes are a common problem. For instance, most of the existing antibodies recognizing Lewis Y show cross-reactivity towards other carbohydrate structures such as Lewis b [Fucα1-4(Fucα1-2Galβ1-3)GlcNAcβ-] that can diminish their therapeutic potential. Furthermore, carbohydrate antigens often generate immune responses of the IgM type which is not considered to be a suitable antibody format for therapy. Using recombinant antibody technologies, class switching from IgM to IgG can be performed. However, considerably functional affinity is lost due to the low intrinsic affinity of carbohydrate-binding antibodies.

Known specific antibodies against Lewis Y are the monoclonal antibodies A70-A/A9 and A70-C/C8, as well as a combined A/A9-C/C8 antibody obtained from chain shuffling (this antibody contains the heavy chain of A70-A/A9 and the light chain of A70-C/C8). However, these are chimeric antibodies having murine variable regions which may cause the problems of non-human antibodies discussed above. Humanization of these antibodies would hence be beneficial. Unfortunately, a humanized antibody often has a lower affinity and specificity for its target antigen than the corresponding non-human or chimeric antibody. This, as the overall three-dimensional structure of the variable regions and in particular the conformation and orientation of the complementarity determining regions (CDRs) may be altered by the replacement of the framework regions. This is especially problematic for antibodies against carbohydrate antigens which generally have a low antigen affinity and specificity. For example, antibody A70-A/A9 shows cross reactivity with Lewis b.

Therefore, there is a need in the art to provide humanized anti-Lewis Y antibodies which have specifically high antigen binding affinity and antigen specificity.

SUMMARY OF THE INVENTION

The present inventors have found humanized anti-Lewis Y antibodies having comparable antigen binding affinity as the parent chimeric antibody from which they are derived. Furthermore, these humanized antibodies exhibit an enhanced antigen specificity in that the cross-reactivity with Lewis b of the parent chimeric antibody is prevented in the humanized form.

Therefore, in a first aspect, the present invention is directed to a humanized antibody which is capable of binding to Lewis Y and which comprises a heavy chain variable region and a light chain variable region, wherein the heavy chain variable region comprises the amino acid sequence of SEQ ID NO: 10, or an amino acid sequence which is at least 90% identical to the amino acid sequence of SEQ ID NO: 10, and wherein the light chain variable region comprises the amino acid sequence of SEQ ID NO: 22, or an amino acid sequence which is at least 90% identical to the amino acid sequence of SEQ ID NO: 22.

In a second aspect, the present invention provides a nucleic acid encoding the antibody according to the invention. Furthermore, in a third aspect an expression cassette or vector comprising the nucleic acid according to the invention and a promoter operatively connected with said nucleic acid and, in a fourth aspect, a host cell comprising the nucleic acid or the expression cassette or vector according to the invention are provided.

In a fifth aspect, the present invention provides a conjugate comprising the antibody according to the invention conjugated to a further agent.

In a sixth aspect, the present invention is directed to a composition comprising the antibody according to the invention, the nucleic acid according to the invention, the expression cassette or vector according to the invention, the host cell according to the invention, or the conjugate according to the invention.

According to a seventh aspect, the invention provides the antibody, the nucleic acid, the expression cassette or vector, the host cell, the composition or the conjugate according to the invention for use in medicine, in particular in the treatment of cancer.

Other objects, features, advantages and aspects of the present invention will become apparent to those skilled in the art from the following description and appended claims.

It should be understood, however, that the following description, appended claims, and specific examples, which indicate preferred embodiments of the application, are given by way of illustration only. Various changes and modifications within the spirit and scope of the disclosed invention will become readily apparent to those skilled in the art from reading the following.

Definitions

As used herein, the following expressions are generally intended to preferably have the meanings as set forth below, except to the extent that the context in which they are used indicates otherwise.

The expression "comprise", as used herein, besides its literal meaning also includes and specifically refers to the expressions "consist essentially of" and "consist of". Thus, the expression "comprise" refers to embodiments wherein the subject-matter which "comprises" specifically listed elements does not comprise further elements as well as embodiments wherein the subject-matter which "comprises" specifically listed elements may and/or indeed does encompass further elements. Likewise, the expression "have" is to be understood as the expression "comprise", also including and specifically referring to the expressions "consist essentially of" and "consist of". The term "consist essentially of", where possible, in particular refers to embodiments wherein the subject-matter comprises 20% or less, in particular 15% or less, 10% or less or especially 5% or less further elements in addition to the specifically listed elements of which the subject-matter consists essentially of.

The term "antibody" in particular refers to a protein comprising at least two heavy chains and two light chains connected by disulfide bonds. Each heavy chain is comprised of a heavy chain variable region (VH) and a heavy chain constant region (CH). Each light chain is comprised of a light chain variable region (VL) and a light chain constant region (CL). The heavy chain-constant region comprises three or—in the case of antibodies of the IgM- or IgE-type—four heavy chain-constant domains (CH1, CH2, CH3 and CH4) wherein the first constant domain CH1 is adjacent to the variable region and may be connected to the second constant domain CH2 by a hinge region. The light chain-constant region consists only of one constant domain. The variable regions can be further subdivided into regions of hypervariability, termed complementarity determining regions (CDRs), interspersed with regions that are more conserved, termed framework regions (FR), wherein each variable region comprises three CDRs and four FRs. The variable regions of the heavy and light chains contain a binding domain that interacts with an antigen. The heavy chain constant regions may be of any type such as γ-, δ-, α-, μ- or ε-type heavy chains. Preferably, the heavy chain of the antibody is a γ-chain. Furthermore, the light chain constant region may also be of any type such as κ- or λ-type light chains. Preferably, the light chain of the antibody is a κ-chain. The terms "γ- (δ-, α-, μ- or ε-) type heavy chain" and "κ- (λ-) type light chain" refer to antibody heavy chains or antibody light chains, respectively, which have constant region amino acid sequences derived from naturally occurring heavy or light chain constant region amino acid sequences, especially human heavy or light chain constant region amino acid sequences. In particular, the amino acid sequence of the constant domains of a γ-type (especially γ1-type) heavy chain is at least 95%, especially at least 98%, identical to the amino acid sequence of the constant domains of a human γ (especially one of the allotypes of the human γ1) antibody heavy chain. Furthermore, the amino acid sequence of the constant domain of a κ-type light chain is in particular at least 95%, especially at least 98%, identical to the amino acid sequence of the constant domain of one of the allotypes of the human κ antibody light chain. The constant regions of the antibodies may mediate the binding of the immunoglobulin to host tissues or factors, including various cells of the immune system (e.g., effector cells) and the first component (C1q) of the classical complement system. The antibody can be e.g. a humanized, human or chimeric antibody.

The antigen-binding portion of an antibody usually refers to full length or one or more fragments of an antibody that retains the ability to specifically bind to an antigen. It has been shown that the antigen-binding function of an antibody can be performed by fragments of a full-length antibody. Examples of binding fragments of an antibody include a Fab fragment, a monovalent fragment consisting of the VL, VH, CL and CH1 domains; a F(ab)$_2$ fragment, a bivalent fragment comprising two Fab fragments, each of which binds to the same antigen, linked by a disulfide bridge at the hinge region; a Fd fragment consisting of the VH and CH1 domains; a Fv fragment consisting of the VL and VH domains of a single arm of an antibody; and a dAb fragment, which consists of a VH domain.

The "Fab part" of an antibody in particular refers to a part of the antibody comprising the heavy and light chain variable regions (VH and VL) and the first domains of the heavy and light chain constant regions (CH1 and CL). In cases where the antibody does not comprise all of these regions, then the term "Fab part" only refers to those of the regions VH, VL, CH1 and CL which are present in the antibody. Preferably, "Fab part" refers to that part of an antibody corresponding to the fragment obtained by digesting a natural antibody with papain which contains the antigen binding activity of the antibody. In particular, the Fab part of an antibody encompasses the antigen binding site or antigen binding ability thereof. Preferably, the Fab part comprises at least the $V_H$ region of the antibody.

The "Fc part" of an antibody in particular refers to a part of the antibody comprising the heavy chain constant regions 2, 3 and—where applicable—4 (CH2, CH3 and CH4). In particular, the Fc part comprises two of each of these regions. In cases where the antibody does not comprise all of these regions, then the term "Fc part" only refers to those of the regions CH2, CH3 and CH4 which are present in the antibody. Preferably, the Fc part comprises at least the CH2 region of the antibody. Preferably, "Fc part" refers to that part of an antibody corresponding to the fragment obtained by digesting a natural antibody with papain which does not contain the antigen binding activity of the antibody. In particular, the Fc part of an antibody is capable of binding to the Fc receptor and thus, e.g. comprises an Fc receptor binding site or an Fc receptor binding ability.

According to the present invention, the term "chimeric antibody" in particular refers to an antibody wherein the constant regions are derived from a human antibody or a human antibody consensus sequence, and wherein at least one and preferably both variable regions are derived from a non-human antibody, e.g. from a rodent antibody such as a mouse antibody.

According to the present invention, the term "humanized antibody" in particular refers to a non-human antibody comprising human constant regions and variable regions which amino acid sequences are modified so as to reduce the immunogenicity of the antibody when administered to the human body. An exemplary method for constructing humanized antibodies is CDR grafting, wherein the CDRs or the specificity determining residues (SDRs) of a non-human antibody are combined with human-derived framework regions. Optionally, some residues of the human framework regions may be backmutated towards the residues of the parent non-human antibody, e.g. for increasing or restoring the antigen binding affinity. Other humanization methods include, for example, resurfacing, superhumanization, and human string content optimization. In the resurfacing methods, only those residues of the non-human framework regions which are positioned at the surface of the antibody are replaced by residues present in corresponding human antibody sequences at said position. Superhumanization essentially corresponds to CDR grafting. However, while during CDR grafting the human framework regions are normally chosen based on their homology to the non-human framework regions, in superhumanization it is the similarity of the CDRs on the basis of which the human framework regions are chosen. In the human string content optimization the differences of the non-human antibody sequence to the human germline sequences is scored and then the antibody is mutated to minimize said score. Furthermore, humanized antibodies can also be obtained by empirical methods wherein large libraries of human framework regions or human antibodies are used to generate multiple antibody humanized candidates and then the most promising candidate is determined by screening methods. Also with the above-described rational approaches several humanized antibody candidates can be generated and then screened, for example for their antigen binding.

The term "human antibody", as used herein, is intended to include antibodies having variable regions in which both the framework and CDR regions are derived from sequences of human origin.

The term "antibody", as used herein, refers in certain embodiments to a population of antibodies of the same kind. In particular, all antibodies of the population of the antibody exhibit the features used for defining the antibody. In certain embodiments, all antibodies in the population of the antibody have the same amino acid sequence. Reference to a specific kind of antibody, such as an anti-Lewis Y antibody, in particular refers to a population of this kind of antibody.

The term "antibody" as used herein also includes fragments and derivatives of said antibody. A "fragment or derivative" of an antibody in particular is a protein or glycoprotein which is derived from said antibody and is capable of binding to the same antigen, in particular to the same epitope as the antibody. Thus, a fragment or derivative of an antibody herein generally refers to a functional fragment or derivative. In particularly preferred embodiments, the fragment or derivative of an antibody comprises a heavy chain variable region. It has been shown that the antigen-binding function of an antibody can be performed by fragments of a full-length antibody or derivatives thereof. Examples of fragments of an antibody include (i) Fab fragments, monovalent fragments consisting of the variable region and the first constant domain of each the heavy and the light chain; (ii) F(ab)$_2$ fragments, bivalent fragments comprising two Fab fragments linked by a disulfide bridge at the hinge region; (iii) Fd fragments consisting of the variable region and the first constant domain CH1 of the heavy chain; (iv) Fv fragments consisting of the heavy chain and light chain variable region of a single arm of an antibody; (v) scFv fragments, Fv fragments consisting of a single polypeptide chain; (vi) (Fv)$_2$ fragments consisting of two Fv fragments covalently linked together; (vii) a heavy chain variable domain; and (viii) multibodies consisting of a heavy chain variable region and a light chain variable region covalently linked together in such a manner that association of the heavy chain and light chain variable regions can only occur intermolecular but not intramolecular. Derivatives of an antibody in particular include antibodies which bind to the same antigen as the parent antibody, but which have a different amino acid sequence than the parent antibody from which it is derived. These antibody fragments and derivatives are obtained using conventional techniques known to those with skill in the art.

A target amino acid sequence is "derived" from or "corresponds" to a reference amino acid sequence if the target amino acid sequence shares a homology or identity over its entire length with a corresponding part of the reference amino acid sequence of at least 75%, more preferably at least 80%, at least 85%, at least 90%, at least 93%, at least 95%, at least 97%, at least 98% or at least 99%. The "corresponding part" means that, for example, framework region 1 of a heavy chain variable region (FRH1) of a target antibody corresponds to framework region 1 of the heavy chain variable region of the reference antibody. In particular embodiments, a target amino acid sequence which is "derived" from or "corresponds" to a reference amino acid sequence is 100% homologous, or in particular 100% identical, over its entire length with a corresponding part of the reference amino acid sequence. A "homology" or "identity" of an amino acid sequence or nucleotide sequence is preferably determined according to the invention over the entire length of the reference sequence or over the entire length of the corresponding part of the reference sequence which corresponds to the sequence which homology or identity is defined. An antibody derived from a parent antibody which is defined by one or more amino acid sequences, such as specific CDR sequences or specific variable region sequences, in particular is an antibody having amino acid sequences, such as CDR sequences or variable region sequences, which are at least 75%, preferably at least 80%, at least 85%, at least 90%, at least 93%, at least 95%, at least 97%, at least 98% or at least 99% homologous or identical, especially identical, to the respective amino acid sequences of the parent antibody. In certain embodiments, the antibody derived from (i.e. derivative of) a parent antibody comprises the same CDR sequences as the parent antibody, but differs in the remaining sequences of the variable regions.

The term "antibody" as used herein also refers to multivalent and multispecific antibodies, i.e. antibody constructs which have more than two binding sites each binding to the same epitope and antibody constructs which have one or more binding sites binding to a first epitope and one or more binding sites binding to a second epitope, and optionally even further binding sites binding to further epitopes.

"Specific binding" preferably means that an agent such as an antibody binds stronger to a target such as an epitope for which it is specific compared to the binding to another target. An agent binds stronger to a first target compared to a second target if it binds to the first target with a dissociation constant ($K_d$) which is lower than the dissociation constant for the second target. Preferably the dissociation constant for the target to which the agent binds specifically is more than 100-fold, 200-fold, 500-fold or more than 1000-fold lower than the dissociation constant for the target to which the agent does not bind specifically. Furthermore, the term "specific binding" in particular indicates a binding affinity between the binding partners with an affinity constant $K_a$ of at least $10^5$ $M^{-1}$, preferably at least $10^6$ $M^{-1}$, more preferably at least $10^7$ $M^{-1}$, for example at least $10^8$ $M^{-1}$. An antibody specific for a certain antigen in particular refers to an antibody which is capable of binding to said antigen with an affinity having a $K_a$ of at least $10^5$ $M^{-1}$, preferably at least $10^6$ $M^{-1}$, more preferably at least $10^7$ $M^{-1}$. For example, the term "anti-Lewis Y antibody" refers to an antibody specifically binding Lewis Y and preferably is capable of binding to Lewis Y with an affinity having a $K_a$ of at least $10^5$ $M^{-1}$, preferably at least $10^6$ $M^{-1}$, more preferably at least $10^7$ $M^{-1}$.

The term "A70-A/A9" as used herein in particular refers to a human/mouse chimeric antibody having the heavy chain and light chain variable region amino acid sequences of SEQ ID NOs: 30 and 31, respectively.

The term "Lewis Y" or "LeY" according to the present invention in particular refers to the carbohydrate structure (or oligosaccharide) Fucα1-2Galβ1-4(Fucα1-3)GlcNAcβ- which in particular may be attached to a support structure or carrier molecule, such as a peptide, protein, lipid or carbohydrate structure. In the above indicated structure, Fuc represents a fucose residue, Gal represents a galactose residue and GlcNAc represents an N-acetylglucosamine residue. "α1-2", "β1-4" and "α1-3" indicate the linkage of the two adjacent monosaccharide residues, especially between carbon atom C1 of the left monosaccharide and carbon atom C2, C4 or C3, respectively, of the right monosaccharide, wherein the linkage at carbon atom C1 can be in α- or β-position (shown in the following scheme for glucose):

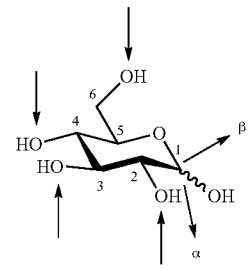

Figure 1:
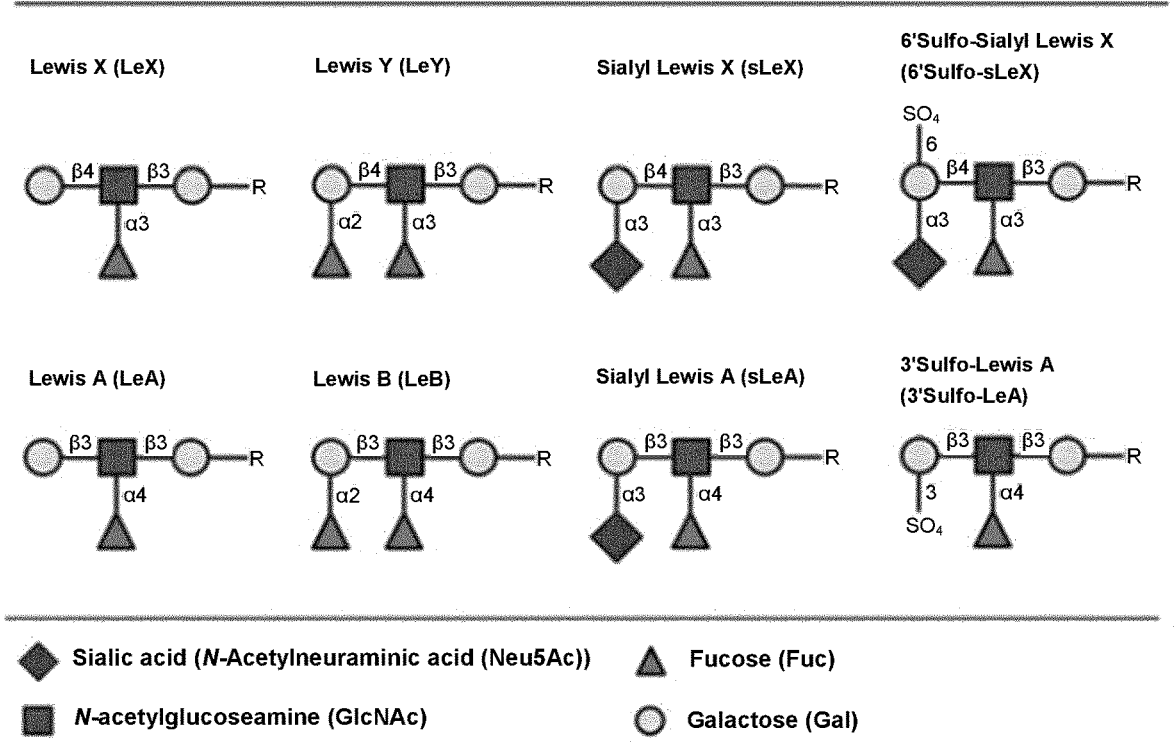

The term "GlcNAcβ-" indicates that the GlcNAc residue at the reducing end of the Lewis Y oligosaccharide is linked in β-configuration to the support structure. A schematic representation of the structures of Lewis Y and related blood group antigens is also shown in FIG. 1.

Lewis Y is a carbohydrate antigen of the human blood group system. It is expressed on many tumors and can be used as tumor-associated or tumor-specific antigen for directed cancer therapy.

The term "sialic acid" in particular refers to any N- or O-substituted derivatives of neuraminic acid. It may refer to both 5-N-acetylneuraminic acid and 5-N-glycolylneuraminic acid, but preferably only refers to 5-N-acetylneuraminic acid.

The terms "glycan", "glycan structure", "carbohydrate", "carbohydrate chain" and "carbohydrate structure" are generally used synonymously herein.

In a "conjugate" two or more compounds are linked together. In certain embodiments, at least some of the properties from each compound are retained in the conjugate. Linking may be achieved by a covalent or non-covalent bond. Preferably, the compounds of the conjugate are linked via a covalent bond. The different compounds of a conjugate may be directly bound to each other via one or more covalent bonds between atoms of the compounds. Alternatively, the compounds may be bound to each other via a chemical moiety such as a linker molecule wherein the linker is covalently attached to atoms of the compounds. If the conjugate is composed of more than two compounds, then these compounds may, for example, be linked in a chain conformation, one compound attached to the next compound, or several compounds each may be attached to one central compound.

The term "nucleic acid" includes single-stranded and double-stranded nucleic acids and ribonucleic acids as well as deoxyribonucleic acids. It may comprise naturally occurring as well as synthetic nucleotides and can be naturally or synthetically modified, for example by methylation, 5'- and/or 3-capping.

The term "expression cassette" in particular refers to a nucleic acid construct which is capable of enabling and regulating the expression of a coding nucleic acid sequence introduced therein. An expression cassette may comprise promoters, ribosome binding sites, enhancers and other control elements which regulate transcription of a gene or translation of an mRNA. The exact structure of expression cassette may vary as a function of the species or cell type, but generally comprises 5-untranscribed and 5- and 3-untranslated sequences which are involved in initiation of transcription and translation, respectively, such as TATA box, capping sequence, CAAT sequence, and the like. More specifically, 5-untranscribed expression control sequences comprise a promoter region which includes a promoter sequence for transcriptional control of the operatively connected nucleic acid. Expression cassettes may also comprise enhancer sequences or upstream activator sequences.

According to the invention, the term "promoter" refers to a nucleic acid sequence which is located upstream (5) of the nucleic acid sequence which is to be expressed and controls expression of the sequence by providing a recognition and binding site for RNA-polymerases. The "promoter" may include further recognition and binding sites for further factors which are involved in the regulation of transcription of a gene. A promoter may control the transcription of a prokaryotic or eukaryotic gene. Furthermore, a promoter may be "inducible", i.e. initiate transcription in response to an inducing agent, or may be "constitutive" if transcription is not controlled by an inducing agent. A gene which is under the control of an inducible promoter is not expressed or only expressed to a small extent if an inducing agent is absent. In the presence of the inducing agent the gene is switched on or the level of transcription is increased. This is mediated, in general, by binding of a specific transcription factor.

The term "vector" is used here in its most general meaning and comprises any intermediary vehicle for a nucleic acid which enables said nucleic acid, for example, to be introduced into prokaryotic and/or eukaryotic cells and, where appropriate, to be integrated into a genome. Vectors of this kind are preferably replicated and/or expressed in the cells. Vectors comprise plasmids, phagemids, bacteriophages or viral genomes. The term "plasmid" as used herein generally relates to a construct of extrachromosomal genetic material, usually a circular DNA duplex, which can replicate independently of chromosomal DNA.

According to the invention, the term "host cell" relates to any cell which can be transformed or transfected with an exogenous nucleic acid. The term "host cells" comprises according to the invention prokaryotic (e.g. *E. coli*) or eukaryotic cells (e.g. mammalian cells, in particular human or hamster cells, yeast cells and insect cells). Particular preference is given to mammalian cells such as cells from humans, mice, hamsters, pigs, goats, or primates. The cells may be derived from a multiplicity of tissue types and comprise primary cells and cell lines. A nucleic acid may be present in the host cell in the form of a single copy or of two or more copies and, in one embodiment, is expressed in the host cell.

The term "patient" means according to the invention a human being, a nonhuman primate or another animal, in particular a mammal such as a cow, horse, pig, sheep, goat, dog, cat or a rodent such as a mouse and rat. In a particularly preferred embodiment, the patient is a human being.

The term "cancer" according to the invention in particular comprises leukemias, seminomas, melanomas, teratomas, lymphomas, neuroblastomas, gliomas, rectal cancer, endometrial cancer, kidney cancer, adrenal cancer, thyroid cancer, blood cancer, skin cancer, cancer of the brain, cervical cancer, intestinal cancer, liver cancer, colon cancer, stomach cancer, intestine cancer, head and neck cancer, gastrointestinal cancer, lymph node cancer, esophagus cancer, colorectal cancer, pancreas cancer, ear, nose and throat (ENT) cancer, bladder cancer, breast cancer, prostate cancer, cancer of the uterus, ovarian cancer and lung cancer and the metastases thereof. The term cancer according to the invention also comprises cancer metastases. The term cancer further also refers to and/or includes cancer stem cells, especially the cancer stem cells of the specific types of cancer listed above.

By "tumor" is meant a group of cells or tissue that is formed by misregulated cellular proliferation. Tumors may show partial or complete lack of structural organization and functional coordination with the normal tissue, and usually form a distinct mass of tissue, which may be either benign or malignant.

By "metastasis" is meant the spread of cancer cells from its original site to another part of the body. The formation of metastasis is a very complex process and normally involves detachment of cancer cells from a primary tumor, entering the body circulation and settling down to grow within normal tissues elsewhere in the body. When tumor cells metastasize, the new tumor is called a secondary or metastatic tumor, and its cells normally resemble those in the original tumor. This means, for example, that, if breast cancer metastasizes to the lungs, the secondary tumor is made up of abnormal breast cells, not of abnormal lung cells. The tumor in the lung is then called metastatic breast cancer, not lung cancer.

The term "pharmaceutical composition" particularly refers to a composition suitable for administering to a human or animal, i.e., a composition containing components which are pharmaceutically acceptable. Preferably, a pharmaceutical composition comprises an active compound or a salt or prodrug thereof together with a carrier, diluent or pharmaceutical excipient such as buffer, preservative and tonicity modifier.

DETAILED DESCRIPTION OF THE INVENTION

The present invention is based on the development of humanized anti-Lewis Y antibodies having an antigen binding affinity similar to that of the corresponding chimeric antibody. The present inventors could further demonstrate that the humanized antibody unexpectedly has an improved antigen specificity. The parent chimeric antibody shows significant binding to Lewis b besides its main specificity for Lewis Y.

Such cross-reactivity is common for antibodies binding to carbohydrate antigens since these antigens are rather small and may be very similar. For example, Lewis Y and Lewis b only differ in that the attachment points of the fucose arm and the fucose-galactose arm at the central GlcNAc residue are switched (see FIG. 1). Nevertheless, the humanized anti-Lewis Y antibodies provided by the present invention surprisingly do not show any cross-reactivity with other carbohydrate antigens, especially not with Lewis b.

In view of these findings, the present invention provides a humanized antibody which is capable of binding to Lewis Y and which comprises a heavy chain variable region and a light chain variable region, wherein the heavy chain variable region comprises the amino acid sequence of SEQ ID NO: 10, or an amino acid sequence which is at least 90% identical to the amino acid sequence of SEQ ID NO: 10, and wherein the light chain variable region comprises the amino acid sequence of SEQ ID NO: 22, or an amino acid sequence which is at least 90% identical to the amino acid sequence of SEQ ID NO: 22.

Furthermore, the humanized antibody may exhibit antigen binding properties similar to those of a reference antibody comprising a heavy chain variable region with the amino acid sequence of SEQ ID NO: 30 and a light chain variable region with the amino acid sequence of SEQ ID NO: 31. Preferably, the reference antibody is the human/mouse chimeric antibody A70-A/A9. In particular, the humanized antibody according to the invention may specifically bind to the same antigen as the reference antibody, and may preferably bind to said antigen with a comparable affinity. That is, the humanized antibody preferably binds to the antigen with an affinity having a dissociation constant which is at most 1000-fold higher than that of the reference antibody, more preferably at most 200-fold higher, at most 100-fold higher, at most 20-fold higher or at most 10-fold higher. Most preferably, the dissociation constant is about the same as that of the reference antibody, in particular being no more than 2-fold higher. Moreover, the humanized antibody preferably shows cross-specificity with the reference antibody comprising a heavy chain variable region with the amino acid sequence of SEQ ID NO: 30 and a light chain variable region with the amino acid sequence of SEQ ID NO: 31. In particular, the humanized antibody is able to block the binding of the reference antibody to Lewis Y if present in a high enough concentration. This may be possible if the binding of the reference antibody to Lewis Y is hindered when the humanized antibody according to the invention is already bound to Lewis Y.

In certain embodiments, the humanized antibody is specifically binding Lewis Y. Especially, the humanized antibody does not show a significant binding affinity for Lewis b and/or does not specifically bind Lewis b. In certain embodiments, the dissociation constant of the humanized antibody for binding to Lewis Y is at least 10-fold lower compared to the dissociation constant of the humanized antibody for binding to Lewis b. In particular, the dissociation constant is at least 20-fold, at least 50-fold or at least 100-fold lower for binding to Lewis Y compared to binding to Lewis b.

In certain embodiments, the heavy chain variable region comprises an amino acid sequence which is at least 93% identical to the amino acid sequence of SEQ ID NO: 10. Especially, the heavy chain variable region comprises an amino acid sequence which is at least 95%, in particular at least 98% identical to the amino acid sequence of SEQ ID NO: 10.

In specific embodiments, the heavy chain variable region of the humanized antibody comprises the complementarity determining regions CDR-H1 having the amino acid sequence of SEQ ID NO: 12 or 13, CDR-H2 having the amino acid sequence of SEQ ID NO: 14 or 15, and CDR-H3 having the amino acid sequence of SEQ ID NO: 16. In particular, the heavy chain variable region comprises an amino acid sequence which is at least 90% identical to the amino acid sequence of SEQ ID NO: 10 and in addition has three specific CDRs having the amino acid sequences of SEQ ID NOs: 12, 14 and 16 or SEQ ID NOs: 13, 15 and 16. Hence, any sequence deviations to SEQ ID NO: 10 are located in the framework regions, but not in the CDRs.

In certain embodiments, the heavy chain variable region comprises the amino acid sequence of SEQ ID NO: 11, or an amino acid sequence which is at least 90% identical to the amino acid sequence of SEQ ID NO: 11. In particular, the heavy chain variable region comprises an amino acid sequence which is at least 93% identical to the amino acid sequence of SEQ ID NO: 11. Especially, the heavy chain variable region comprises an amino acid sequence which is at least 95%, in particular at least 98% identical to the amino acid sequence of SEQ ID NO: 11. In specific embodiments, the heavy chain variable region comprises an amino acid sequence which is at least 90% identical to the amino acid sequence of SEQ ID NO: 11 and in addition has three specific CDRs having the amino acid sequences of SEQ ID NOs: 12, 14 and 16.

Specifically, the humanized antibody may comprise a heavy chain variable region having an amino acid sequence according to any one of SEQ ID NOs: 1 to 9. In particular, the heavy chain variable region has the amino acid sequence according to any one of SEQ ID NOs: 1 to 6, especially SEQ ID NO: 1 or 4, preferably SEQ ID NO: 1. In specific embodiments, the heavy chain variable region comprises an amino acid sequence which is at least 90% identical to the amino acid sequence of SEQ ID NO: 1, especially, at least 93%, at least 95%, or in particular at least 98% identical to the amino acid sequence of SEQ ID NO: 1. In these embodiments, the heavy chain variable region preferably has three specific CDRs having the amino acid sequences of SEQ ID NOs: 12, 14 and 16.

In certain embodiments, the light chain variable region comprises an amino acid sequence which is at least 93% identical to the amino acid sequence of SEQ ID NO: 22. Especially, the light chain variable region comprises an amino acid sequence which is at least 95%, in particular at least 98% identical to the amino acid sequence of SEQ ID NO: 22.

In specific embodiments, the light chain variable region of the humanized antibody comprises the complementarity determining regions CDR-L1 having the amino acid sequence of SEQ ID NO: 24 or 25, CDR-L2 having the amino acid sequence of SEQ ID NO: 26 or 27, and CDR-L3 having the amino acid sequence of SEQ ID NO: 28 or 29. In particular, the light chain variable region comprises an amino acid sequence which is at least 90% identical to the amino acid sequence of SEQ ID NO: 18 and in addition has three specific CDRs having the amino acid sequences of SEQ ID NOs: 24, 26 and 28 or SEQ ID NOs: 25, 27 and 29. Hence, any sequence deviations to SEQ ID NO: 22 are located in the framework regions, but not in the CDRs.

In certain embodiments, the light chain variable region comprises the amino acid sequence of SEQ ID NO: 23, or an amino acid sequence which is at least 90% identical to the amino acid sequence of SEQ ID NO: 23. In particular, the light chain variable region comprises an amino acid sequence which is at least 93% identical to the amino acid sequence of SEQ ID NO: 23. Especially, the light chain variable region comprises an amino acid sequence which is at least 95%, in particular at least 98% identical to the amino acid sequence of SEQ ID NO: 23. In specific embodiments, the light chain variable region comprises an amino acid sequence which is at least 90% identical to the amino acid sequence of SEQ ID NO: 23 and in addition has three specific CDRs having the amino acid sequences of SEQ ID NOs: 24, 26 and 28.

Specifically, the humanized antibody may comprise a light chain variable region having an amino acid sequence according to any one of SEQ ID NOs: 17 to 21. In particular, the light chain variable region has the amino acid sequence according to SEQ ID NO: 17 or 18, especially SEQ ID NO: 17. In specific embodiments, the light chain variable region comprises an amino acid sequence which is at least 90% identical to the amino acid sequence of SEQ ID NO: 17, especially, at least 93%, at least 95%, or in particular at least 98% identical to the amino acid sequence of SEQ ID NO: 17.

In specific embodiments, the humanized antibody has a heavy chain variable region which comprises an amino acid sequence which is at least 90% identical to the amino acid sequence of SEQ ID NO: 10 and in addition has three specific CDRs having the amino acid sequences of SEQ ID NOs: 12, 14 and 16 or SEQ ID NOs: 13, 15 and 16; and a light chain variable region which comprises an amino acid sequence which is at least 90% identical to the amino acid sequence of SEQ ID NO: 22 and in addition has three specific CDRs having the amino acid sequences of SEQ ID NOs: 24, 26 and 28 or SEQ ID NOs: 25, 27 and 29. In certain preferred embodiments, the humanized antibody comprises a heavy chain variable region comprising the amino acid sequence of SEQ ID NO: 10 and a light chain variable region comprising the amino acid sequence of SEQ ID NO: 22.

In specific embodiments, the humanized antibody has a heavy chain variable region which comprises an amino acid sequence which is at least 90% identical to the amino acid sequence of SEQ ID NO: 11 and in addition has three specific CDRs having the amino acid sequences of SEQ ID NOs: 12, 14 and 16; and a light chain variable region which comprises an amino acid sequence which is at least 90% identical to the amino acid sequence of SEQ ID NO: 23 and in addition has three specific CDRs having the amino acid sequences of SEQ ID NOs: 24, 26 and 28. In certain preferred embodiments, the humanized antibody comprises a heavy chain variable region comprising the amino acid sequence of SEQ ID NO: 11 and a light chain variable region comprising the amino acid sequence of SEQ ID NO: 23.

In certain embodiments, the humanized antibody comprises a heavy chain variable region comprising an amino acid sequence selected from the group consisting of SEQ ID NO: 1 to 7 and 9, especially 1 to 6, and a light chain variable region comprising the amino acid sequence of SEQ ID NO: 17 or 18, especially 17. In particular, the humanized antibody comprises a heavy chain variable region comprising the amino acid sequence of SEQ ID NO: 1 or 4, and a light chain variable region comprising the amino acid sequence of SEQ ID NO: 17. Especially, the humanized antibody comprises a heavy chain variable region comprising the amino acid sequence of SEQ ID NO: 1, and a light chain variable region comprising the amino acid sequence of SEQ ID NO: 17. In other embodiments, the humanized antibody comprises a heavy chain variable region comprising the amino acid sequence of SEQ ID NO: 8, and a light chain variable region comprising the amino acid sequence of SEQ ID NO: 19.

In preferred embodiments, the humanized antibody comprises an Fc region. The humanized antibody may especially be a whole antibody. The humanized antibody may be of any isotype, and in particular is an IgG-type antibody, especially IgG1, IgG2 or IgG4. In specific embodiments, the humanized antibody is an IgG1-type antibody. The humanized antibody in particular is capable of binding to one or more human Fc receptors, especially human Fcγ receptors such as Fcγ receptor IIIa.

In further embodiments, the humanized anti-Lewis Y antibody is a fragment of an antibody. Especially the fragment is selected from the group consisting of (i) Fab fragments; (ii) F(ab)$_2$ fragments; (iii) Fd fragments; (iv) Fv fragments; (v) scFv fragments; and (vi) (Fv)$_2$ fragments. In certain embodiments, the humanized anti-Lewis Y antibody does not comprise an Fc region.

In certain embodiment, the humanized anti-Lewis Y antibody is glycosylated, especially N-glycosylated. In particular, the humanized antibody has a glycosylation site in the second constant domain of the heavy chain (CH2). An antibody normally has two heavy chains having identical amino acid sequences. Hence, the humanized antibody preferably has at least two glycosylation sites, one in each of its two CH2 domains. This glycosylation site in particular is at an amino acid position corresponding to amino acid position 297 of the heavy chain according to the Kabat numbering and has the amino acid sequence motive Asn Xaa Ser/Thr wherein Xaa may be any amino acid except proline. The N-linked glycosylation at Asn297 is conserved in mammalian IgGs as well as in homologous regions of other antibody isotypes. Due to optional additional amino acids which may be present in the variable region or other sequence modifications, the actual position of this conserved glycosylation site may vary in the amino acid sequence of the antibody.

In preferred embodiments, the humanized anti-Lewis Y antibody does not comprise N-glycolyl neuraminic acids (NeuGc) or detectable amounts of NeuGc. Furthermore, the humanized antibody preferably also does not comprise Galili epitopes (Galα1,3-Gal structures) or detectable amounts of the Galili epitope. In particular, the relative amount of glycans carrying NeuGc and/or Galα1,3-Gal structures is less than 0.1% or even less than 0.02% of the total amount of glycans attached to the Fc part of the humanized antibodies in the antibody population.

In other embodiments, the humanized anti-Lewis Y antibody is not glycosylated at its CH2 domains. In these embodiments, the CH2 domain of the antibody may be mutated, for example by substituting the asparagine residue at position 297 of the heavy chain (or a corresponding position) by any other amino acid, for example alanine or glutamine. Antibodies lacking glycosylation at the CH2 domain have reduced binding to Fcγ receptors and thus, reduced effector functions. In further embodiments, the humanized anti-Lewis Y antibody may have other or additional amino acid substitutions which reduce Fc receptor binding, including, for example, Leu235Glu ("LE mutation"), Leu234Ala/Leu235Ala ("LALA" mutation), Ser228Pro/Leu235Glu ("SPLE" mutation), Leu234Ala/Leu235Ala/Pro329Gly ("LALA-PG" mutation) and combinations thereof.

The humanized anti-Lewis Y antibody is preferably recombinantly produced in a host cell. Hence, the humanized antibody in particular is a monoclonal antibody. The host cell used for the production of the humanized antibody may be any host cells which can be used for antibody production. Suitable host cells are in particular eukaryotic host cells, especially mammalian host cells. Exemplary host cells include yeast cells such as *Pichia pastoris* cell lines, insect cells such as SF9 and SF21 cell lines, plant cells, bird cells such as EB66 duck cell lines, rodent cells such as CHO, NS0, SP2/0 and YB2/0 cell lines, and human cells such as HEK293, PER.C6, CAP, CAP-T, AGE1.HN, Mutz-3 and KG1 cell lines.

In certain embodiments, the humanized anti-Lewis Y antibody is produced recombinantly in a human cell line, in particular in a human myeloid leukemia cell line. Preferred human cell lines which can be used for production of the anti-Lewis Y antibody as well as suitable production procedures are described in WO 2008/028686 A2. In a specific embodiment, the humanized anti-Lewis Y antibody is obtained by expression in a human myeloid leukemia cell line selected from the group consisting of NM-H9D8, NM-H9D8-E6 and NM-H9D8-E6Q12. These cell lines were deposited under the accession numbers DSM ACC2806 (NM-H9D8; deposited on Sep. 15, 2006), DSM ACC2807 (NM-H9D8-E6; deposited on Oct. 5, 2006) and DSM ACC2856 (NM-H9D8-E6Q12; deposited on Aug. 8, 2007) according to the requirements of the Budapest Treaty at the Deutsche Sammlung von Mikroorganismen und Zellkulturen (DSMZ), Inhoffenstraße 7B, 38124 Braunschweig (DE) by Glycotope GmbH, Robert-Rössle-Str. 10, 13125 Berlin (DE). NM-H9D8 cells provide a glycosylation pattern with a high degree of sialylation, a high degree of bisecting GlycNAc, a high degree of galactosylation and a high degree of fucosylation. NM-H9D8-E6 and NM-H9D8-E6Q12 cells provide a glycosylation pattern similar to that of NM-H9D8 cells, except that the degree of fucosylation is very low. Other suitable cell lines include K562, a human myeloid leukemia cell line present in the American Type Culture Collection (ATCC CCL-243), CHO cells, as well as cell lines derived from the aforementioned. In specific embodiments, the humanized anti-Lewis Y antibody is produced recombinantly in CHO cells, especially in CHO dhfr cells.

In specific embodiments, the humanized anti-Lewis Y antibody is provided as conjugate comprising the antibody conjugated to a further agent such as a detectable marker or a therapeutically active substance. The humanized antibody can be conjugated to one or more further agents. If more than one further agent is present in the conjugate, these further agents may be identical or different, and in particular are all identical. Conjugation of the further agent to the humanized antibody can be achieved using any methods known in the art. The further agent may be covalently, in particular by fusion or chemical coupling, or non-covalently attached to the antibody. In certain embodiments, the further agent is covalently attached to the humanized antibody, especially via a linker moiety. The linker moiety may be any chemical entity suitable for attaching the further agent to the humanized antibody.

The further agent preferably is useful in therapy, diagnosis, prognosis and/or monitoring of a disease, in particular cancer. For example, the further agent may be selected from the group consisting of radionuclides, chemotherapeutic agents, antibodies, bispecific antibodies or antibody fragments, in particular those of different species and/or different specificity than the humanized anti-Lewis Y antibody, enzymes, interaction domains, detectable labels, toxins, cytolytic components, immunomodulators, immunoeffectors, cytokines, chemokines, MHC class I or class II antigens, and liposomes.

In certain embodiments, the further agent is a polypeptide or protein. This polypeptide or protein may in particular be fused to a polypeptide chain of the humanized antibody. In certain embodiments, the further agent being a polypeptide or protein is fused to the C terminus of an antibody light chain of the humanized antibody. In embodiments wherein the humanized antibody comprises two antibody light chains, a further agent being a polypeptide or protein may be fused to the C terminus of each of the two antibody light chains. In further embodiments, the further agent being a polypeptide or protein is fused to the C terminus of an antibody heavy chain of the humanized antibody. In embodiments wherein the humanized antibody comprises two antibody heavy chains, a further agent being a polypeptide or protein may be fused to the C terminus of each of the two antibody heavy chains. The further agents may be identical or different and in particular have the same amino acid sequence. In embodiments wherein the humanized antibody does not comprise one or more light chains and one or more heavy chains, for example in cases where the humanized antibody is an antibody fragment, a further agent being a polypeptide or protein may be fused to the C terminus or the N terminus of a polypeptide chain of the humanized antibody. Suitable examples of such further agents being a polypeptide or protein may be selected from the group consisting of cytokines, chemokines, antibodies, antigen binding fragments, enzymes, and interaction domains.

In certain embodiments, the further agent being a polypeptide or protein is a checkpoint antibody which blocks and/or triggers activating signals. Examples of respective targets include CD40, CD3, CD137 (4-1BB), OX40, GITR, CD27, CD278 (ICOS), CD154 (CD40 ligand), CD270 (HVEM) and CD258 (LIGHT) as activating targets, CTLA4, PD1, CD80, CD244, A2AR, B7-H3 (CD276), B7-H4 (VTCN1), BTLA, IDO, KIR, LAG3, TIM-3, VISTA and phosphatidylserine as inhibitory targets, and their respective ligands such as PDL1. In further embodiment the further agent being a polypeptide or protein is an anti-cancer antibody directed to a tumor-associated antigen. Exemplary suitable tumor targets and anti-cancer antibodies which may be used as fusion partner are described below with respect to combination therapies.

In further embodiments, the further agent being a polypeptide or protein is an immunomodulatory compound such as a chemokine, cytokine or growth factor. Suitable cytokines in this respect include interferons such as interferon-α, interferon-β and interferon-γ, and interleukins such as IL-15. Suitable growth factors include G-CSF and GM-CSF.

In specific embodiments, the further agent being a polypeptide or protein is an antigen receptor, especially a T cell receptor or a T cell co-receptor, or a part and/or chimera thereof. In particular, the humanized anti-Lewis Y antibody is fused to a transmembrane domain and an intracellular T-cell signaling domain, forming a chimeric antigen receptor (CAR). The intracellular domain is in particular derived from one or more T cell receptors or co-receptors. Optionally, the CAR further comprises a hinge region between the humanized antibody and the transmembrane domain.

In these embodiments, the humanized anti-Lewis Y antibody in particular is a single chain antibody fragment which comprises the heavy chain variable region and the light chain variable region in one polypeptide chain, especially a scFv fragment. The hinge region may for example be based on a hinge region or membrane-proximal region of a member of the immunoglobulin superfamily. Exemplary hinge regions include those derived from IgG, CD8 and CD28. The transmembrane domain may be a hydrophobic alpha helix that spans the cell membrane. It is for example derived from CD28. The intracellular T-cell signaling domain in particular comprises the cytoplasmic domain of the (chain of the T cell receptor. In addition, the intracellular T-cell signaling domain may comprise further domains of co-stimulatory proteins of T cells. Exemplary further domains include signaling domains from CD28, CD27, CD134 (OX40), and CD137 (4-1BB).

An exemplary CAR may comprise, from N terminus to C terminus, (i) the humanized anti-Lewis Y antibody in the form of a scFv fragment, (ii) an extracellular hinge region derived from CD8, (iii) a transmembrane domain derived from CD28, (iv) a cytoplasmic signaling domain derived from CD28, and (v) a signaling domain derived from the T cell receptor ζ-chain.

Alternatively, the humanized anti-Lewis Y antibody, especially in single chain format such as scFv, may be fused N terminally to a CD3 chain of the T cell receptor complex, especially the CD3ε chain, to form a chimeric antigen receptor. Or the humanized anti-Lewis Y antibody, especially in single chain format such as scFv, may be fused to a binding domain which is capable of specifically binding to naturally occurring or engineered receptors on T cells or NK cells.

In certain embodiments, the further agent is a cytotoxic or chemotherapeutic agent, especially a cytotoxin. Specific examples of chemotherapeutic agents that can be conjugated as further agent include alkylating agents such as cisplatin, antimetabolites, plant alkaloids and terpenoids, vinca alkaloids, podophyllotoxin, taxanes such as taxol, topoisomerase inhibitors such as irinotecan and topotecan, antineoplastics such as doxorubicin or microtubule inhibitors such as auristatins and maytansin/maytansinoids.

The chemotherapeutic agent may in particular be selected from a group consisting of a V-ATPase inhibitor, a pro-apoptotic agent, a Bcl2 inhibitor, an MCL1 inhibitor, a HSP90 inhibitor, an IAP inhibitor, an mTor inhibitor, a microtubule stabilizer, a microtubule destabilizer, an auristatin, a dolastatin, a maytansin, a maytansinoid, amatoxin, a methionine aminopeptidase, an inhibitor of nuclear export of proteins CRM1, a DPPIV inhibitor, proteasome inhibitors, inhibitors of phosphoryl transfer reactions in mitochondria, a protein synthesis inhibitor, a kinase inhibitor, a CDK2 inhibitor, a CDK9 inhibitor, a kinesin inhibitor, an HDAC inhibitor, a topoisomerase I inhibitor, a DNA damaging agent, a DNA alkylating agent, a DNA intercalator, a DNA minor groove binder, a DHFR inhibitor, an inhibitor of microtubule formation, a stabilizer of microtubuli, a stabilizer of actin, a topoisomerase II inhibitor, a platinum compound, a ribosome inhibitor, an RNA polymerase II inhibitor and a bacterial toxin. In specific embodiments, the chemotherapeutic agent attached to the anti-LeY antibody is selected from the group consisting of an auristatin, a maytansinoid, a topoisomerase I inhibitor, a DNA damaging agent, a DNA alkylating agent and a DNA minor groove binder.

In some embodiments of the chemotherapeutic agent is a maytansin or maytansinoid. Specific examples of maytansinoids useful for conjugation include maytansinol, $N^{2'}$-deacetyl-$N^{2'}$-(3-mercapto-1-oxopropyl)-maytansine (DM1), $N^{2'}$-deacetyl-$N^{2'}$-(4-mercapto-1-oxopentyl)-maytansine (DM3), and $N^{2'}$-deacetyl-$N^{2'}$-(4-methyl-4-mercapto-1-oxopentyl)-maytansine (DM4). In particular, DM1 or DM4 is attached to the anti-LeY antibody. In some embodiments, the chemotherapeutic agent attached to the anti-LeY antibody is an auristatin, in particular monomethyl auristatin F (MMAF), monomethyl auristatin E (MMAE) or auristatin T. In some embodiments, the chemotherapeutic agent attached to the anti-LeY antibody is a DNA minor groove binder, in particular pyrrolobenzodiazepine (PBD), pyrrolobenzodiazepine dimer (PBD dimer), duocarmycin, duocarmycin-hydroxybenzamide-azaindole (DUBA), seco-duocarmycin-hydroxybenzamide-azaindole (seco-DUBA) or doxorubicin. In some embodiments, the chemotherapeutic agent attached to the anti-LeY antibody is a DNA alkylating agent, in particular indolinobenzodiazepine or oxazolidinobenzodiazepine. In some embodiments, the chemotherapeutic agent attached to the anti-LeY antibody is a DNA damaging agent, in particular calicheamicin. In some embodiments, the chemotherapeutic agent attached to the anti-LeY antibody is a topoisomerase I inhibitor, in particular camptothecin and its derivatives such as 7-ethyl-10-hydroxycamptothecin (SN-38), (S)-9-dimethylaminomethyl-10-hydroxycamptothecin (topotecan), (1S,9S)-1-amino-9-ethyl-5-fluoro-1,2,3,9,12,15-hexahydro-9-hydroxy-4-methyl-10H,13H-benzo[de] pyrano [3',4':6,7]indolizino[1,2-b]quinoline-10,13-dione (Exatecan (DX-8951f)) and DXd. In some embodiments, the chemotherapeutic agent attached to the anti-LeY antibody is an inhibitor of microtubule formation, in particular a tubulysin, an ansamitocin, podophyllotoxin or vinblastine. In some embodiments, the chemotherapeutic agent attached to the anti-LeY antibody is a stabilizer of microtubuli, in particular paclitaxel or an epothilone. In some embodiments, the chemotherapeutic agent attached to the anti-LeY antibody is a stabilizer of actin, in particular a phallotoxin. In some embodiments, the chemotherapeutic agent attached to the anti-LeY antibody is a topoisomerase II inhibitor, in particular teniposide, XK469, razoxane, amsacrine, idarubicin or mebarone. In some embodiments, the chemotherapeutic agent attached to the anti-LeY antibody is a platinum compound, in particular cisplatin, carboplatin, oxaliplatin, nedaplatin, triplatin tetranitrate, phenanthriplatin, picoplatin or sattraplatin. In some embodiments, the chemotherapeutic agent attached to the anti-LeY antibody is a ribosome inhibitor, in particular ricin, saporin, abrin, diphtheria toxin or exotoxin A. In some embodiments, the chemotherapeutic agent attached to the anti-LeY antibody is an RNA polymerase II inhibitor, in particular an amatoxin, such as, for example, amanitin. In some embodiments, the chemotherapeutic agent attached to the anti-LeY antibody is a bacterial toxin, in particular anthrax toxin. Suitable antibody drug conjugates are also described in EP 16 151 774.3 and LU 92659, to which is explicitly referred to herewith.

Further suitable toxins which may be conjugated to the humanized anti-Lewis Y antibody are described below with respect to combination therapies.

In a further aspect, the present invention provides a nucleic acid encoding the humanized anti-Lewis Y antibody. The nucleic acid sequence of said nucleic acid may have any nucleotide sequence suitable for encoding the antibody. However, preferably the nucleic acid sequence is at least partially adapted to the specific codon usage of the host cell or organism in which the nucleic acid is to be expressed, in particular the human codon usage. The nucleic acid may be double-stranded or single-stranded DNA or RNA, preferably double-stranded DNA such as cDNA or single-stranded RNA such as mRNA. It may be one consecutive nucleic acid molecule or it may be composed of several nucleic acid molecules, each coding for a different part of the humanized antibody.

If the humanized antibody is composed of more than one different amino acid chain, such as a light chain and a heavy chain, the nucleic acid may, for example, be a single nucleic acid molecule containing several coding regions each coding for one of the amino acid chains of the antibody, preferably separated by regulatory elements such as IRES elements in order to generate separate amino acid chains, or the nucleic acid may be composed of several nucleic acid molecules wherein each nucleic acid molecule comprises one or more coding regions each coding for one of the amino acid chains of the antibody. Alternatively, the nucleic acid may be a single nucleic acid molecule containing one coding region which encodes for the heavy chain and the light chain, separated by a self-cleaving peptide such as a 2A peptide, and/or a linker peptide containing a protease recognition site such as a furin recognition site. In addition to the coding regions encoding the humanized antibody, the nucleic acid may also comprise further nucleic acid sequences or other modifications which, for example, may code for other proteins, may influence the transcription and/or translation of the coding region(s), may influence the stability or other physical or chemical properties of the nucleic acid, or may have no function at all.

In certain embodiments, the nucleic acid is a viral vector which can be used for the infection of human cells. These viral vectors may be suitable, for example, for therapy of humans, e.g. by directing infection and or replication of the virus to disease cells such as tumor cells, or be modifying T cells in embodiments where the humanized antibody is in the form of a chimeric antigen receptor to obtain CAR T cells.

In a further aspect, the present invention provides an expression cassette or vector comprising a nucleic acid according to the invention and a promoter operatively connected with said nucleic acid. In addition, the expression cassette or vector may comprise further elements, in particular elements which are capable of influencing and/or regulating the transcription and/or translation of the nucleic acid, the amplification and/or reproduction of the expression cassette or vector, the integration of the expression cassette or vector into the genome of a host cell, and/or the copy number of the expression cassette or vector in a host cell. Suitable expression cassettes and vectors comprising respective expression cassettes for expressing antibodies are well known in the prior art and thus, need no further description here.

Furthermore, the present invention provides a host cell comprising the nucleic acid according to the invention or the expression cassette or vector according to the invention. The host cell may be any host cell. It may be an isolated cell or a cell comprised in a tissue. Preferably, the host cell is a cultured cell, in particular a primary cell or a cell of an established cell line, preferably a tumor-derived cell. Preferably, it is a bacterial cell such as *E. coli*, a yeast cell such as a *Saccharomyces* cell, in particular *S. cerevisiae*, an insect cell such as a Sf9 cell, or a mammalian cell, in particular a human cell such as a tumor-derived human cell, a hamster cell such as CHO, or a primate cell. In a preferred embodiment of the invention the host cell is derived from human myeloid leukaemia cells. Preferably, it is selected from the following cells or cell lines: K562, KG1, MUTZ-3, CHO or a cell or cell line derived therefrom, or a mixture of cells or cell lines comprising at least one of those aforementioned cells. The host cell is preferably selected from the group consisting of NM-H9D8, NM-H9D8-E6, NM H9D8-E6Q12, and a cell or cell line derived from anyone of said host cells, or a mixture of cells or cell lines comprising at least one of those aforementioned cells. These cell lines and their properties are described in detail in the PCT-application WO 2008/028686 A2. In preferred embodiments, the host cell is optimized for expression of glycoproteins, in particular antibodies, having a specific glycosylation pattern. Preferably, the codon usage in the coding region of the nucleic acid according to the invention and/or the promoter and the further elements of the expression cassette or vector are compatible with and, more preferably, optimized for the type of host cell used. Preferably, the humanized antibody is produced by a host cell or cell line as described above.

In another aspect, the present invention provides a composition comprising the humanized antibody, the nucleic acid, the expression cassette or vector, the host cell, or the conjugate. The composition may also contain more than one of these components. Furthermore, the composition may comprise one or more further components selected from the group consisting of solvents, diluents, and excipients Preferably, the composition is a pharmaceutical composition. In this embodiment, the components of the composition preferably are all pharmaceutically acceptable. The composition may be a solid or fluid composition, in particular a—preferably aqueous—solution, emulsion or suspension or a lyophilized powder.

The humanized anti-Lewis Y antibody or the conjugate thereof in particular is useful in medicine, in particular in therapy, diagnosis, prognosis and/or monitoring of a disease, in particular a disease as described herein, for example cancer and infections, preferably cancer. Therefore, in a further aspect, the invention provides the humanized antibody, the nucleic acid, the expression cassette or vector, the host cell, the conjugate, or the composition for use in medicine. Preferably, the use in medicine is a use in the treatment, prognosis, diagnosis and/or monitoring of a disease such as, for example, diseases associated with abnormal cell growth such as, for example, cancer, or infectious diseases. Infectious diseases in particular include viral infections and bacterial infections, especially infections with a virus or bacterium that carries Lewis Y on its surface. Exemplary infections include infections with *Helicobacter* bacteria.

In a preferred embodiment, the disease is cancer, especially epithelial cancer, in particular advanced epithelial cancer. Preferably the cancer is selected from the group consisting of lung cancer, colon cancer, colorectal cancer, breast cancer, ovarian cancer, gastric cancer, leukemia such as acute myelogenous leukemia, lymphoma such as multiple myeloma, head and neck cancer, pancreatic cancer, liver cancer, prostate cancer and bladder cancer, especially non-small cell lung cancer, colon cancer, breast cancer and ovarian cancer.

In certain embodiments, the disease to be treated is a disease associated with abnormal cell growth such as cancer. The cancer is Lewis Y positive and in particular comprises cancer cells which carry Lewis Y on their cell surface. In specific embodiments, the humanized anti-Lewis Y antibody is used in combination with another anti-cancer therapeutic agent. Said further therapeutic agent may be any known anti-cancer drug and in particular may be an antibody against a cancer antigen. Suitable antibodies for combination with the humanized anti-Lewis Y antibody include anti-EGFR antibodies such as cetuximab (Erbitux), tomuzotuximab, panitumomab (Vectibix) and nimotuzumab (Theraloc), anti-HER2 antibodies such as trastuzumab (Herceptin), timigutuzumab and pertuzumab; anti-VEGF antibodies such as bevacizumab (Avastin) and vanuzizumab; anti-CD52 antibodies such as alemtuzumab (Campath); anti-CD30 antibodies such as brentuximab (Adcetris); anti-CD33 antibodies such as gemtuzumab (Mylotarg); anti-CD20 antibodies such as rituximab (Rituxan, Mabthera), tositumomab (Bexxar) and ibritumomab (Zevalin); anti-CTLA4 antibodies such as ipilimumab and tremelimumab, anti-PD1/PD-L1 antibodies such as pembrolizumab, nivolumab, atezolizumab, and avelumab, antibodies against TNF and TNFR superfamily members such as urelumab, MED16469, TRX518, and varilumab; CSF1R antibodies such as emactuzumab; anti-B7-H3 antibodies such as enoblituzumab; anti-LAG3 antibodies; anti-4-1BB antibodies; anti-ICOS antibodies; and anti-OX-40 antibodies.

Further anti-cancer therapeutic agents which may be combined with the humanized anti-Lewis Y antibody and optionally one or more further antibodies may be selected from the group consisting of taxanes such as paclitaxel (Taxol), docetaxel (Taxotere) and SB-T-1214; cyclophosphamide; lapatinib; erlotinib; imatinib; pazopanib; capecitabine; cytarabine; vinorelbine; gemcitabine; anthracyclines such as daunorubicin, doxorubicin, epirubicin, idarubicin, valrubicin and mitoxantrone; aromatase inhibitors such as aminoglutethimide, testolactone (Teslac), anastrozole (Arimidex), letrozole (Femara), exemestane (Aromasin), vorozole (Rivizor), formestane (Lentaron), fadrozole (Afema), 4-hydroxyandrostenedione, 1,4,6-androstatrien-3,17-dione (ATD) and 4-androstene-3,6,17-trione (6-OXO); topoisomerase inhibitors such as irinotecan, topotecan, camptothecin, lamellarin D, etoposide (VP-16), teniposide, doxorubicin, daunorubicin, mitoxantrone, amsacrine, ellipticines, aurintricarboxylic acid and HU-331; platinum based chemotherapeutic agents such as cis-diamminedichloroplatinum(II) (cisplatin), cis-diammine(1,1-cyclobutanedicarboxylato)platinum(II) (carboplatin) and [(1R,2R)-cyclohexane-1,2-diamine](ethanedioato-O,O')platinum(II) (oxaliplatin); antimetabolites, in particular antifolates such as methotrexate, pemetrexed, raltitrexed and pralatrexate, pyrimidine analogues such as fluoruracil, gemcitabine, floxuridine, 5-fluorouracil and tegafur-uracil, and purine analogues; and inhibitors of the enzyme poly ADP ribose polymerase (PARP inhibitors) such as olaparib, rucaparib, niraparib and talazoparib. Further suitable toxins which may be used in combination with the humanized anti-Lewis Y antibody are described above with respect to agents which may be conjugated to the humanized antibody.

Treatment with the humanized anti-Lewis Y antibody may further be combined with immunostimulatory agents, cytokines, chemokines, radiation therapy, vaccines such as protein, peptide or RNA vaccines, B-Raf inhibitors such as vemurafenib, dexametasone, protease inhibitors such as bortezomib, and lenalidomide.

For use in the treatment of cancer wherein the cells express Lewis Y, the humanized antibody may be coupled to a further agent as described above, wherein the further agent preferably is a cytotoxic agent such as a radionuclide or a cytotoxin. Exemplary cytotoxic agents are described above. Cytotoxic agents also include precursor compounds which only develop cytotoxic activity upon activation, e.g. by irradiation with light or enzymatic reaction inside the body. One or more of the anti-cancer therapeutic agents described above may also be used as further agent for coupling to the humanized anti-Lewis Y antibody. Furthermore, the humanized antibody may be engineered so as to enhance its ability to activate the patient's immune response, in particular the ability to activate ADCC (antibody-dependent cell-mediated cytotoxicity) and/or CDC (complement dependent cytotoxicity). For example, this may be achieved by optimizing the amino acid sequence and/or the glycosylation pattern of the antibody, in particular of its constant regions.

For use as detection agent in diagnosis, prognosis and/or monitoring of a disease, the humanized antibody preferably is coupled to a labeling agent which is capable of producing a detectable signal. In particular, said labeling agent may be a radionuclide, a fluorophore or an enzyme.

FIGURES

FIG. 1 shows a schematic representation of the Lewis carbohydrate antigen family. The Lewis antigens are a related set of glycans that carry fucose in an alpha 1-3 (Lewis X, Y) or an alpha 1-4 (Lewis A, B) linkage to the GlcNAc monosaccharide.

FIG. 2 shows the results of antigen ELISA assays. Different humanized anti-Lewis Y antibody variants were tested for their binding to Lewis Y, Lewis b and Globo H. A high O.D. signal indicates strong binding of the antibody to the antigen. A: Binding of antibody variants at 25 ng/mL to Lewis Y (LeY), Lewis b (Leb) and Globo H. B: Binding of antibody variants at 25 ng/mL and 12.5 ng/mL to Lewis Y. C: Binding of antibody variants at 100 ng/mL, 50 ng/mL and 25 ng/mL to Lewis b. D: Binding of antibody variants at 100 ng/mL, 50 ng/mL and 25 ng/mL to Globo H. Control (ctrl.+): parent human/mouse chimeric antibody AA9.

Figure 3:
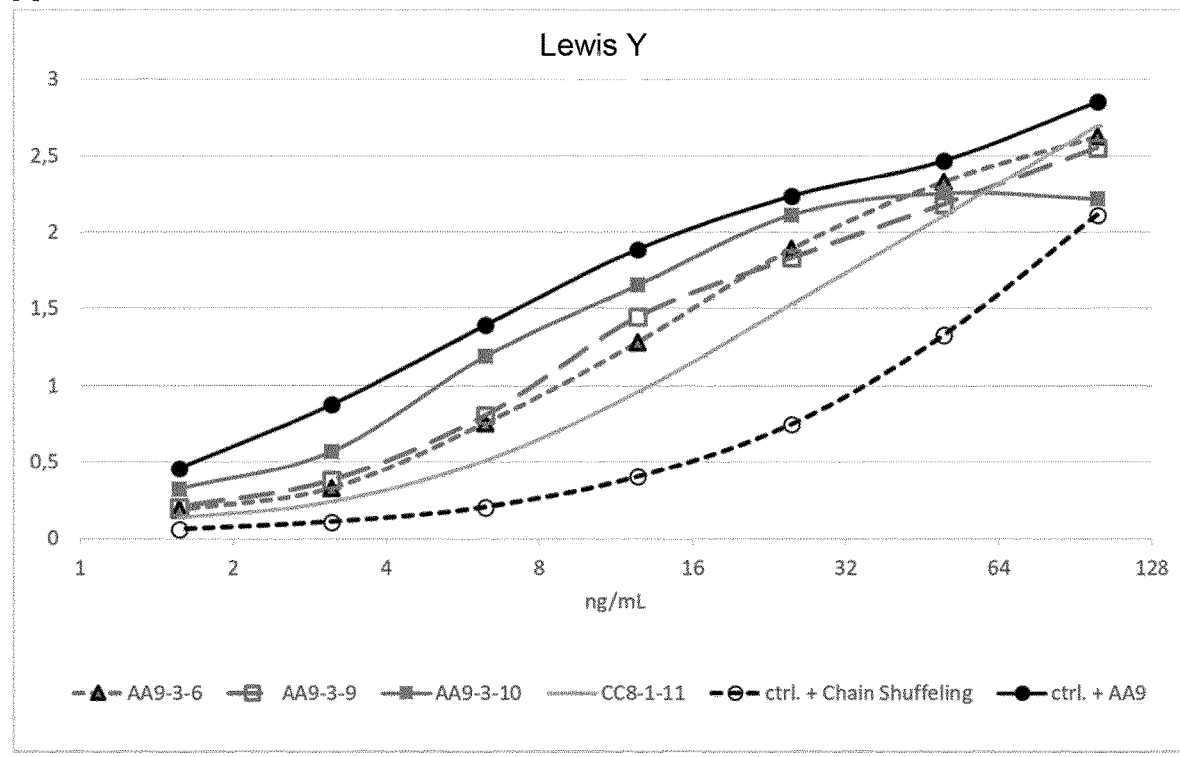
Figure 3:
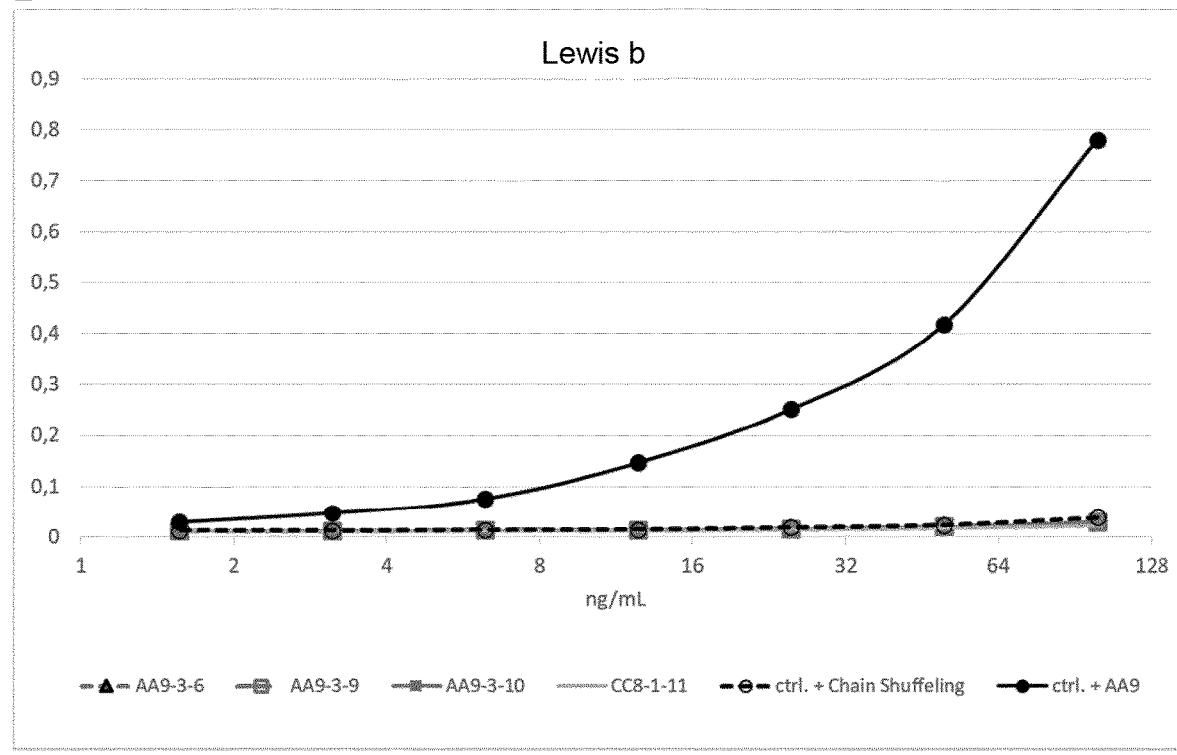

FIG. 3 shows the results of antigen ELISA assays. Binding curves for different humanized anti-Lewis Y antibody variants to Lewis Y (A) and Lewis b (B) were determined. Control 1 (ctrl.+AA9): parent human/mouse chimeric antibody AA9. Control 2 (ctrl.+Chain shuffling): chain shuffling antibody comprising the heavy chain of human/mouse chimeric antibody AA9 and the light chain of human/mouse chimeric antibody CC8.

Figure 4:
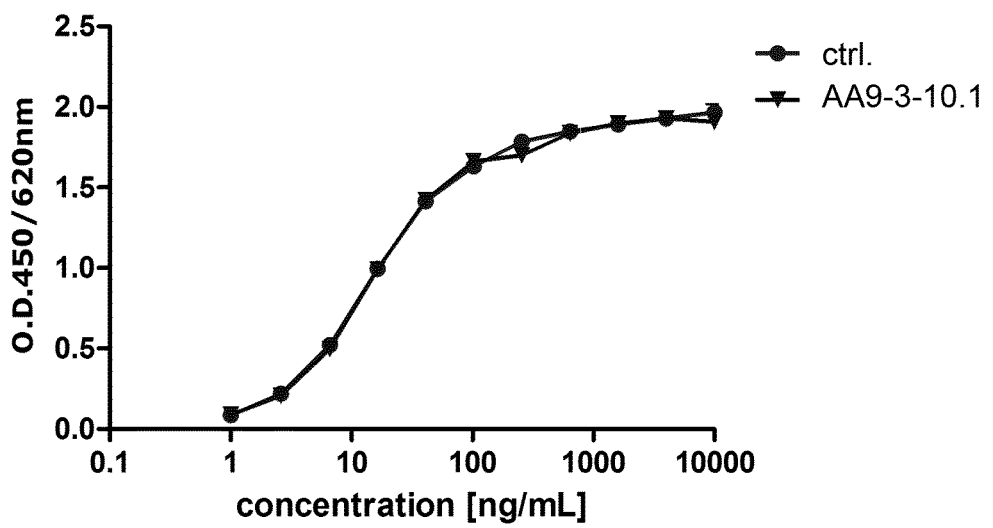
Figure 4:
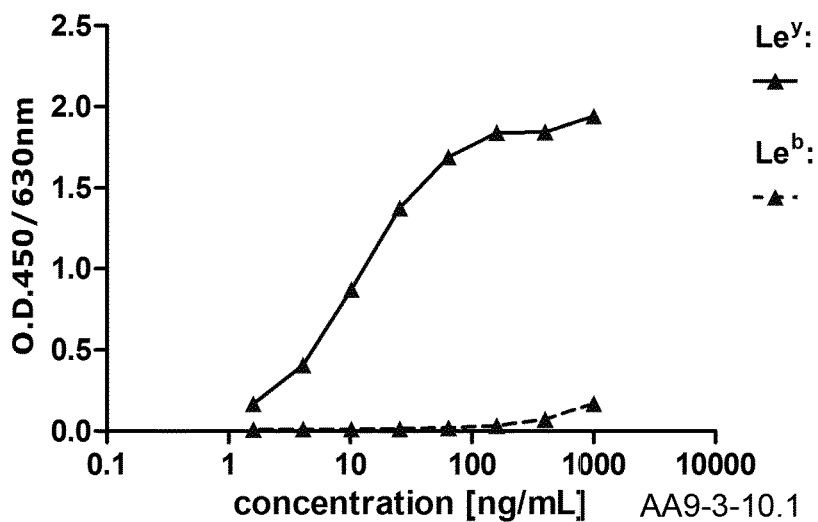

FIG. 4 shows the results of antigen ELISA assays. Binding curves for the humanized anti-Lewis Y antibody AA9-3-10.1 to Lewis Y and Lewis b were determined. Control (ctrl.): parent human/mouse chimeric antibody AA9.

Figure 5:

FIG. 5 shows the results of antigen ELISA assays. Binding of the humanized anti-Lewis Y antibody AA9-3-10.1 (humanized AA9) and the parent human/mouse chimeric antibody AA9 (chimeric AA9) to different carbohydrate antigens was tested at an antibody concentration of 50 ng/mL.

FIG. 6 shows the results of antigen ELISA assays. Different sequence-optimized versions of the humanized anti-Lewis Y antibody AA9-3-10 were tested for their binding to Lewis Y and Lewis b. A high O.D. signal indicates strong binding of the antibody to the antigen. A: Binding of antibody variants at 50 ng/mL to Lewis Y (LeY) and Lewis b (Leb). B: Binding of antibody variants at 50 ng/mL and 25 ng/mL to Lewis Y. C: Binding of antibody variants at 100 ng/mL and 50 ng/mL to Lewis b. Control (pos.-ctrl.-Set2 128+129): parent human/mouse chimeric antibody AA9.

Figure 7:
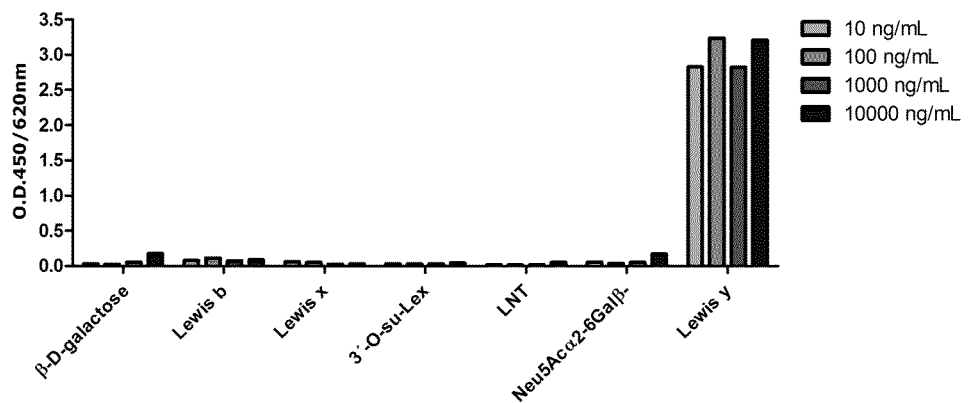
Figure 7:
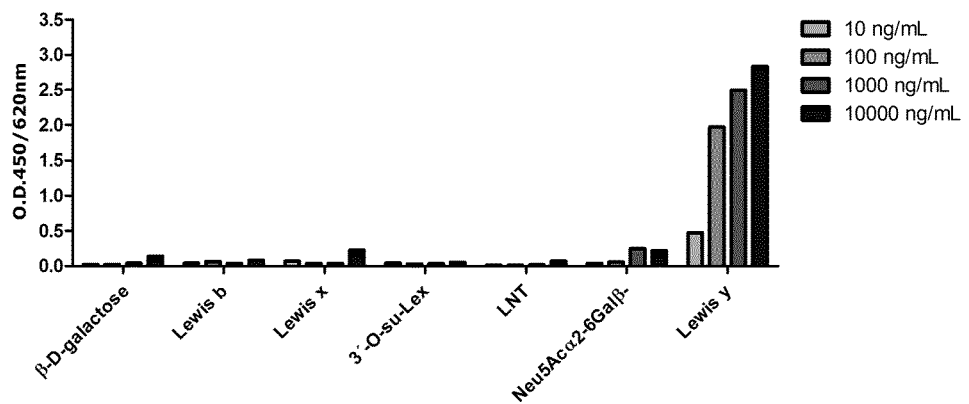
Figure 7:
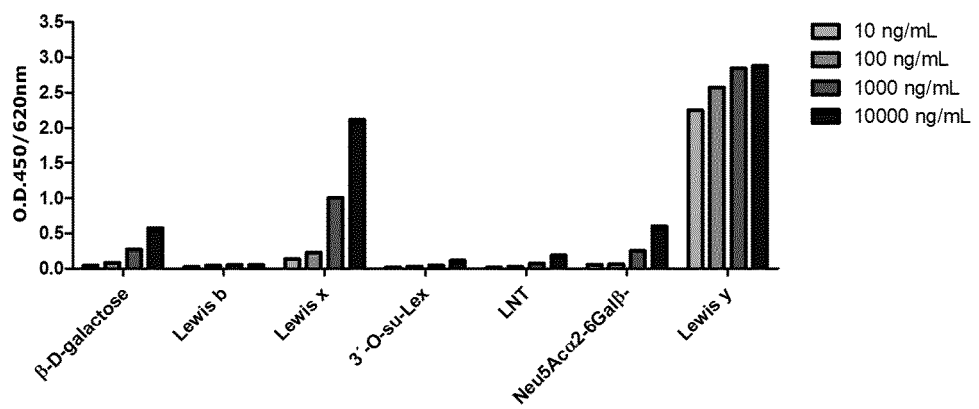

FIG. 7 shows the results of antigen ELISA assays. Different anti-Lewis Y antibodies were tested for their specificity by analyzing their binding to Lewis Y and other, related carbohydrate antigens. A: humanized anti-Lewis Y antibody AA9-3-10.1; B: anti-Lewis Y antibody h3S193; C: anti-Lewis Y antibody BR96.

Figure 8:
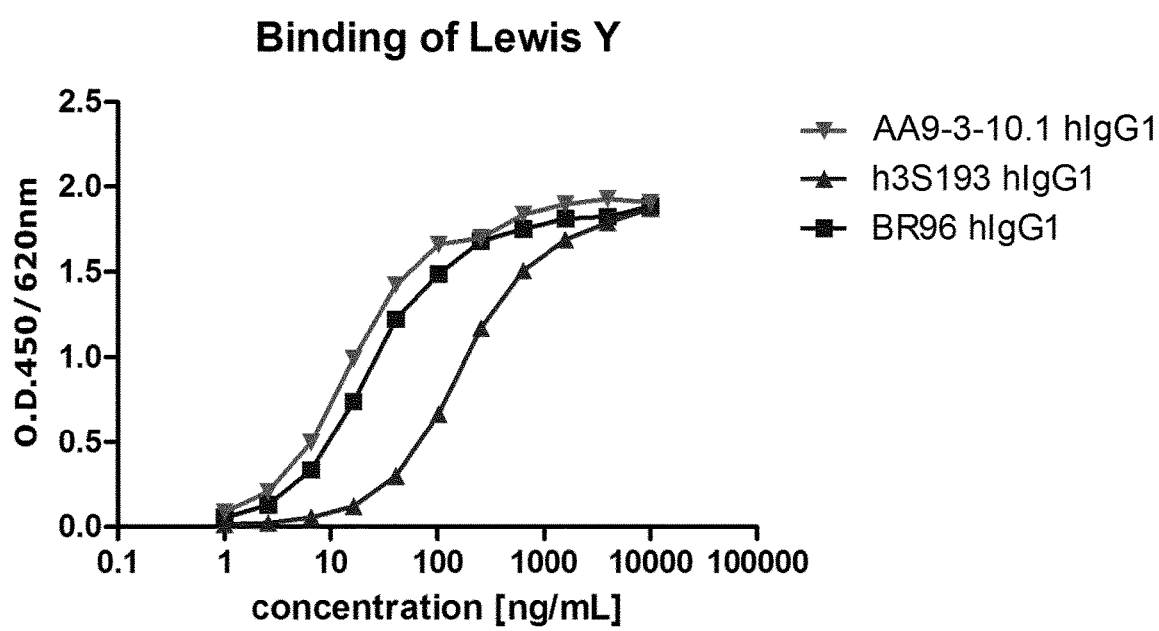

FIG. 8 shows the results of antigen ELISA assays. Binding curves for the anti-Lewis Y antibodies AA9-3-10.1, h3S193 and BR96 to Lewis Y were determined.

Figure 9:
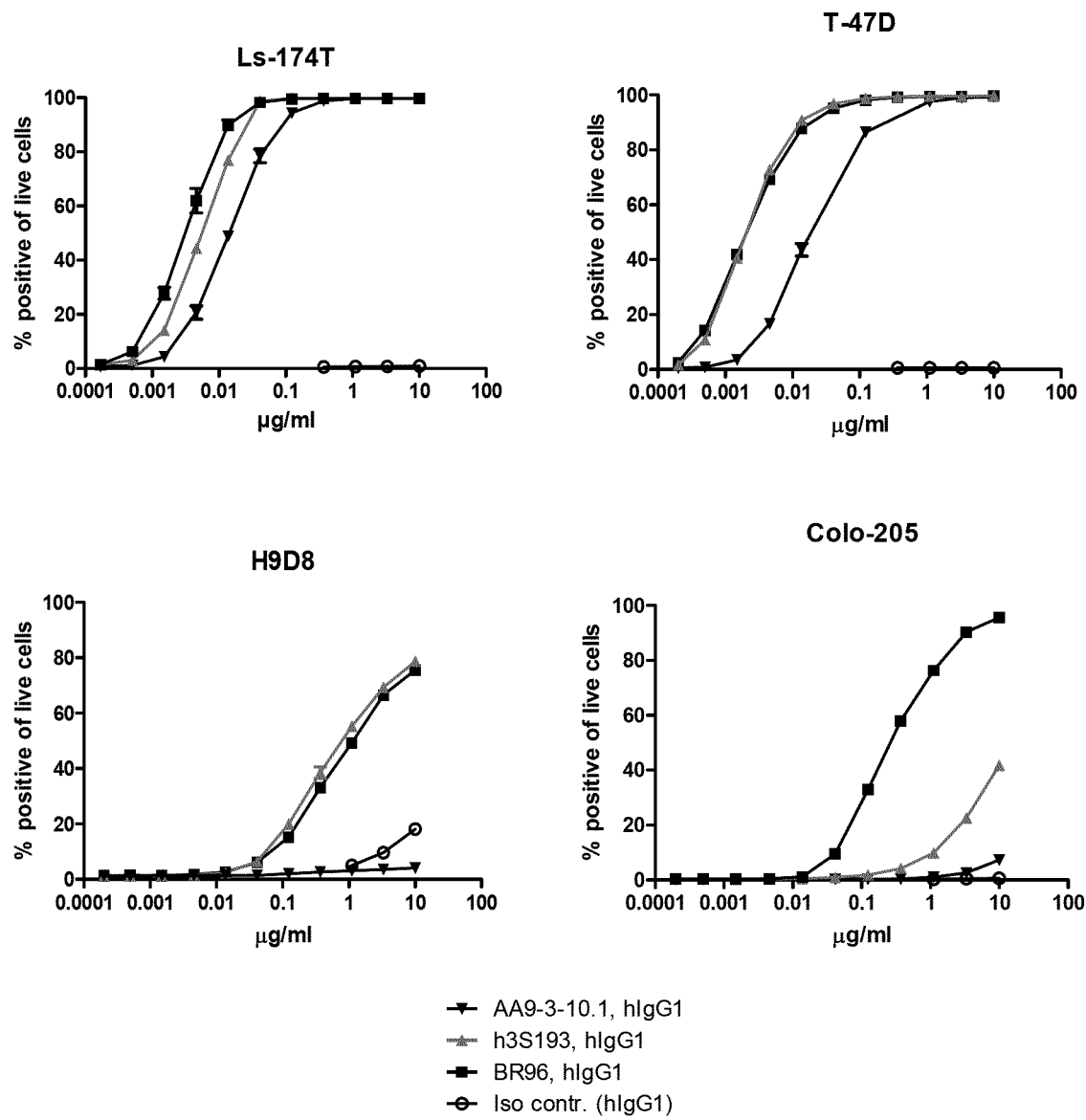

FIG. 9 shows binding of humanized anti-Lewis Y antibody variant AA9-3-10.1, BR96 and h3S193 (as hIgG1) to the tumor cell lines Ls-174T, T-47D, H9D8 and Colo-205. Irrelevant hIgG1 was used as a negative control. Binding is reported as percentage of antibody-positive cells of total live cells.

Figure 10:
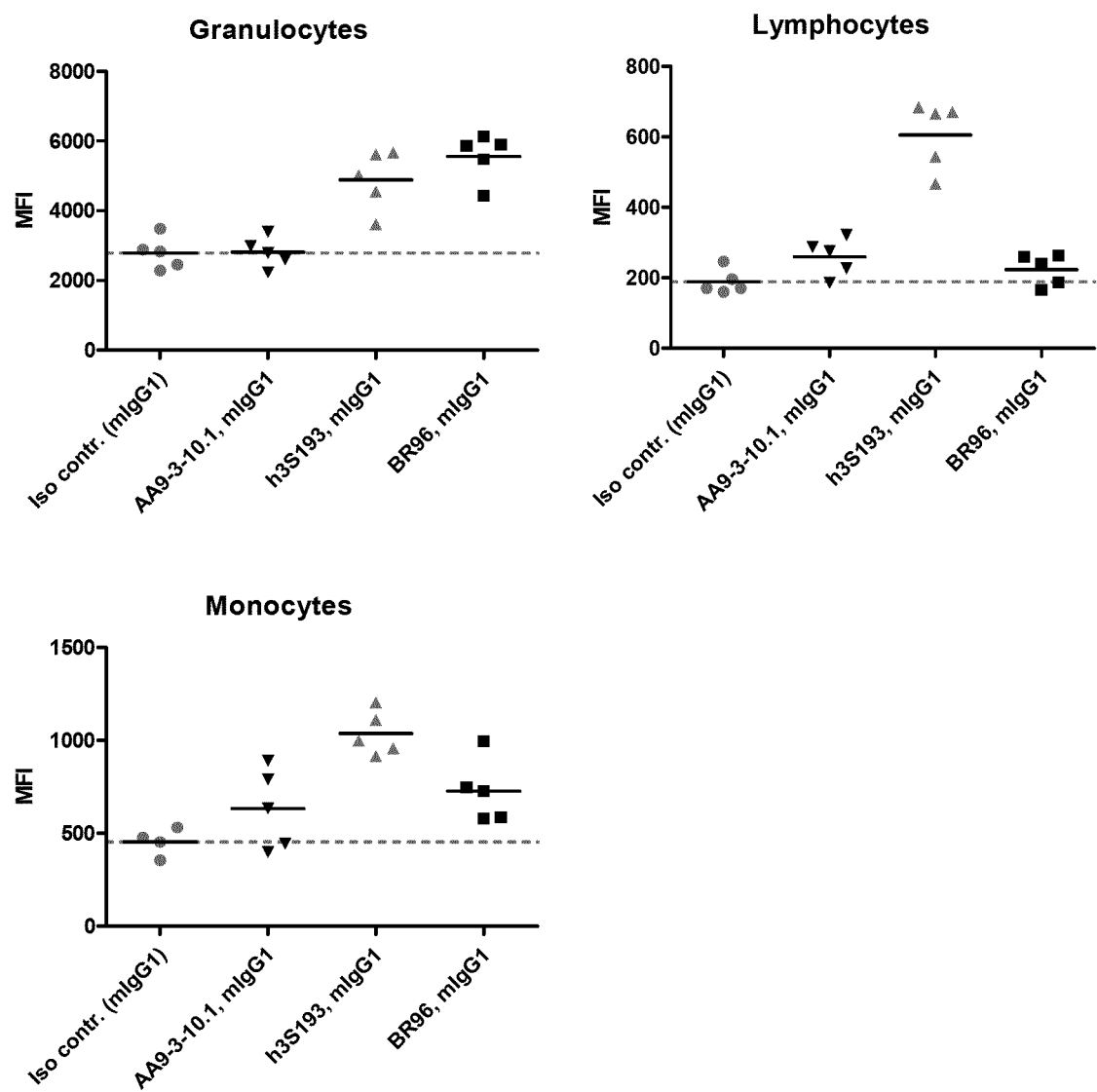

FIG. 10 shows binding of humanized anti-Lewis Y antibody variant AA9-3-10.1, BR96 and h3S193 (as mIgG1) to leukocytes isolated from five healthy donors. Irrelevant hIgG1 was used as a reference. Binding to granulocytes, lymphocytes and monocytes is reported as median fluorescence intensity (MFI).

Figure 11:
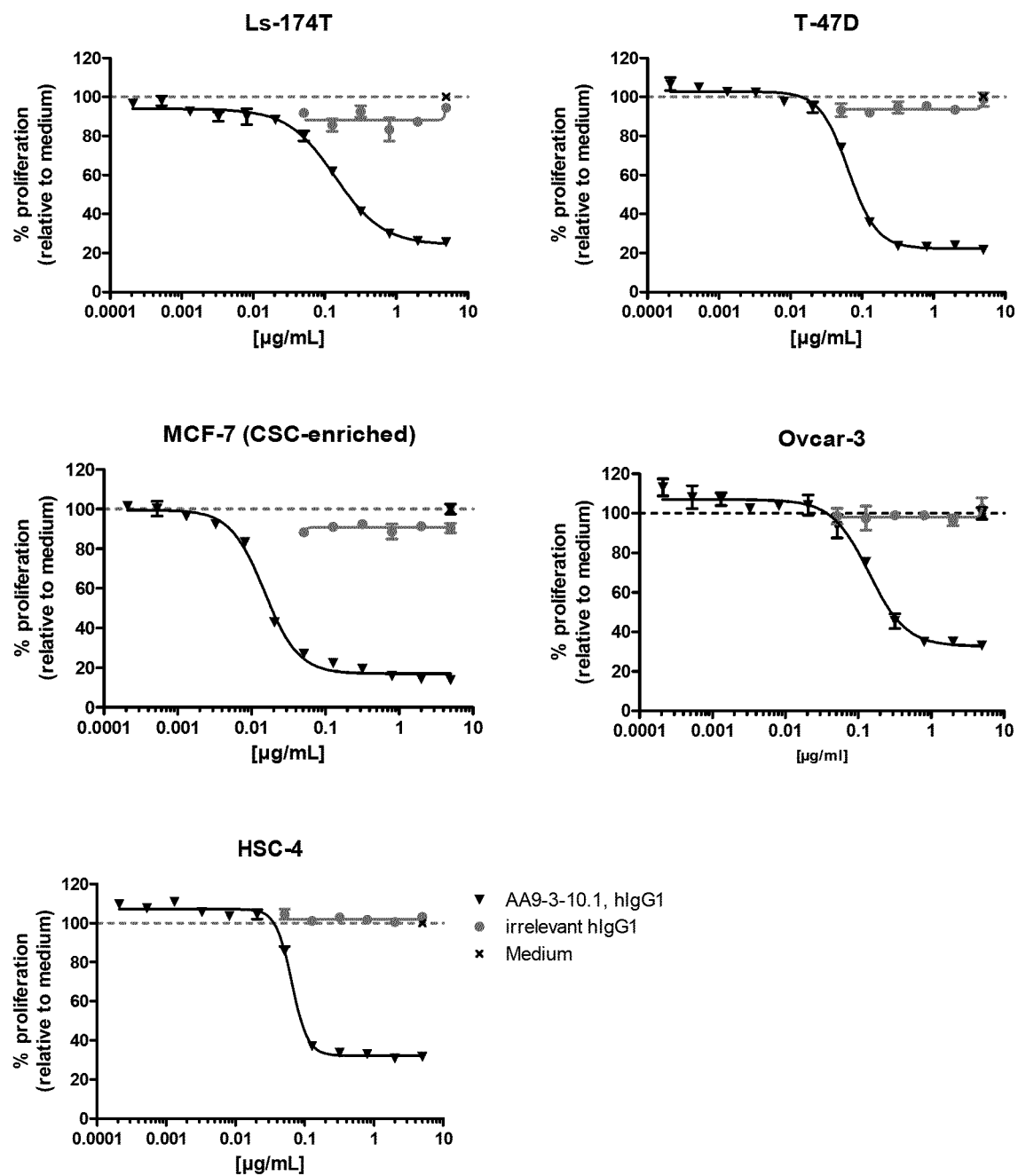

FIG. 11 shows proliferation inhibition experiments of toxin-coupled AA9-3-10.1 (as hIgG1) and isotype control with different tumor cell lines. Proliferation is reported as percentage proliferation relative to medium control.

EXAMPLES

Example 1: Humanization of the Murine Heavy and Light Chain Variable Regions of Anti-LeY Antibodies The nucleic acid sequences coding for the murine heavy and light chain variable regions of two monoclonal anti-LeY antibodies (AA9: SEQ ID NOs: 30 and 31; CC8: SEQ ID NO: 32) were ligated to the genomic sequences of the human constant γ1 region (CH) and the human constant K region (CL), respectively.

On the basis of these chimeric clones, humanized antibodies were constructed. To this end, point mutations were introduced into the nucleic acid sequences of the murine framework regions of VH and VL in order to generate the corresponding human framework regions. The target human framework regions were selected from a human germ line antibody library. In particular, the most related framework regions were chosen from the library depending on their overall sequence similarity and their CDR loop classification. All data obtained were considered to design a set of different variable sequences of humanized variable light and variable heavy chains of both parent murine antibodies. Some of the variants contain back-mutations to the murine sequence on critical positions. The humanized variants of the light chain variable region were cloned in a κ-chain vector and the humanized variants of the heavy chain variable region were cloned in a γ1-chain vector.

Antibodies comprising different combinations of the obtained heavy and light chains were produced and screened for their expression and LeY binding profile. The following humanized antibody heavy and light chains variable regions were selected for further analysis.

TABLE 1

| heavy chain variable region | SEQ ID NO | parent murine antibody | light chain variable region | SEQ ID NO | parent murine antibody |
|---|---|---|---|---|---|
| VH6 | 9 | AA9 | VL1 | 19 | CC8 |
| VH9 | 7 | AA9 | VL2 | 20 | CC8 |
| VH10 | 6 | AA9 | VL3 | 17 | AA9 |
| VH11 | 8 | AA9 | VL6 | 21 | CC8 |
| VH10.1 | 1 | AA9 | VL7 | 18 | AA9 |
| VH10.2 | 2 | AA9 | | | |
| VH10.3 | 3 | AA9 | | | |
| VH10.4 | 4 | AA9 | | | |
| VH10.5 | 5 | AA9 | | | |

Example 2: Binding of the Humanized Antibody Variants to Different Carbohydrate Antigens Following expression of the different constructs in NM-H9D8 cells, the titer of the humanized antibody variants was determined and their concentration adjusted. Then, the humanized antibodies were analyzed in an antigen ELISA for binding to Lewis Y, Lewis b and Globo H. Briefly, antigens (coupled to polyacrylamide) were coated to 96-well MaxiSorp plates (Nunc ThermoScientific) overnight. Unspecific binding was blocked and test samples were added at different concentrations. Afterwards, anti-human IgG-Fc POD secondary antibody was added, followed by TMB substrate reaction. Bound antibodies were determined by measurement at 450/630 nm using an EnSpire 2300 multilabel reader (PerkinElmer) or at 450/620 nm using a Tecan SPARK plate reader.

All variants showed significant binding to Lewis Y similar to that of the parental chimeric antibody. Furthermore, binding to Globo H was negative for all antibodies. However, surprisingly the selected humanized antibody variants showed significantly reduced cross-reactivity towards Lewis b (see FIGS. 2, 3 and 4).

Humanized antibody variants AA9-3-6 (comprising VL3 and VH6), AA9-3-9 (comprising VL3 and VH9), AA9-3-10 (comprising VL3 and VH10) and CC8-1-11 (comprising VL1 and VH11) were further analyzed for their fine specificity using an antigen ELISA with Lewis Y, Galα1,2-Gal and β-N-acetyl-D-glucosamine-6-sulfate. The analyzed humanized antibodies showed strong, highly specific binding to Lewis Y, but no significant binding to other carbohydrate antigens. Binding to the following carbohydrate antigens was tested at an antibody concentration of 50 ng/mL (see also FIG. 5):

TABLE 2

| | |
|---|---|
| Lac-di-Nac | SiaLe$^x$ |
| GlcNAcβ1-3Galβ- | 6'-SL |
| Tk | β-N-acetyl-D-glucosamine-6-sulfate |
| GalNAcβ1-4Galβ1-4Glcβ- | 3'-O-su-Le$^a$ |
| A [type 2]- | 3'-OSO3-Le$^x$ |
| B [type ]- | 3'-su-LacNAc |
| Galα1-3'Lac | 3'-su-Le$^c$ |
| GlcNAcβ1-2' TF | melibiose |
| Galα4GlcNAc | Galα1-3'LacNAc |
| Neu5Acβ | [Sia]$_2$ |
| α-D-glucose | [Sia]$_3$ |
| α-D-galactose | Gal2βGal |
| β-D-galactose | 6-O-su-LacNAc |
| α-D-mannose | core 2 |
| α-D-mannose-6-phosphate | H [type 4] |
| α-L-fucose | LNT |
| β-N-acetyl-D-glucosamine | LNnT |
| α-N-acetyl-D-galactosamine [T$_n$] | Neu5Ac6Gal |
| β-N-acetyl-D-galactosamine | GM4 |
| Man$_3$ | A$_{tri}$ |
| β-D-galactose-3-sulfate | B$_{tri}$ |
| α-N-acetylneuraminic acid | A$_{di}$ |
| 3'SLN | B$_{di}$ |
| Pk, Gb3, GbOse3 | H [type 2] |
| Taβ | 6'-O-su-LacNAc |
| Galβ3Gal | H$_{di}$ |
| Le$^a$ | GlcNAcβ1-3Galβ1-4Glcβ- |
| Le$^b$ | di-GalNAcβ |
| Le$^d$/H type 1 | core 3 |
| Le$^c$ | core 6 |
| Le$^x$ | core 4 |
| Le$^y$ | Sia$_2$ TF |
| La$^c$ | 6-SiaTF |
| LacNAc | 11-OS, YDS |
| TF | 9-OS |
| Fucα3GlcNAc | 7-OS |
| Fs-2 | 3,6-SiaT$_n$ |
| core 5 | 6'SLN |
| T $_{aa?}$ | maltose |
| 3'-SiaLe$^c$ | β-D-glucose |
| T$_{ββ}$ | Fucα4GlcNAc, L$^c$ |
| [GlcNAc]$_2$ | Galα2Gal |
| SiaT$_n$ | SiaT$_n$ |
| H [type 3]/Globo H | GlcNAcβ1-4GalNAcα- |
| 3'-SL | 3'-O-su-TF |
| SiaLe$^a$ | 3-SiaT$_n$ |

Example 3: Generation of Further Humanization Variants Based on Antibody AA9-3-10

Humanized antibody variant AA9-3-10 (comprising VL3 and VH10) was selected as best candidate for further optimization of the humanized VH sequence. The following humanized antibodies were generated as described in Example 1:

TABLE 3

| antibody | heavy chain variable region | SEQ ID NO | light chain variable region | SEQ ID NO |
|---|---|---|---|---|
| AA9-3-10.1 | VH10.1 | 1 | VL3 | 17 |
| AA9-3-10.2 | VH10.2 | 2 | VL3 | 17 |
| AA9-3-10.3 | VH10.3 | 3 | VL3 | 17 |
| AA9-3-10.4 | VH10.4 | 4 | VL3 | 17 |
| AA9-3-10.5 | VH10.5 | 5 | VL3 | 17 |

Binding of these humanized antibody variants to Lewis Y and Lewis b was analyzed as described in Example 2. All antibody variants show strong, highly specific binding to Lewis Y. No significant binding to Lewis b could be detected (see FIG. 6).

Example 4: Comparison of Antigen Binding and Specificity of the Humanized Variant AA9-3-10.1 with Known Anti-LeY Antibodies Binding specificity of the humanized antibody variant AA9-3-10.1 to different, closely related carbohydrate antigens (βD-galactose, Lewis b, Lewis X, 3'-O-su-Lewis X, lacto-N-tetraose (LNT), Neu5Aca2-5Galβ, and Lewis Y) was compared to that of the known antibodies h3S193 and BR96.

Briefly, antigens (coupled to polyacrylamide) were coated to 96-well MaxiSorp plates (Nunc ThermoScientific) overnight. Unspecific binding was blocked and test samples were added at different concentrations. Afterwards, anti-human IgG (H+L) POD secondary antibody was added, followed by TMB substrate reaction. Bound antibodies were determined by measurement at 450/630 nm using an EnSpire 2300 multilabel reader (PerkinElmer) or at 450/620 nm using a Tecan SPARK plate reader.

Humanized antibody variant AA9-3-10.1 shows stronger binding to Lewis Y and a significantly improved specificity. Binding of h3S193 to Lewis Y is much lower at low antibody concentrations and BR96 shows significant binding to βD-galactose and Lewis X. Furthermore, both h3S193 and BR96 bind Neu5Aca2-5Galβ at higher concentrations (see FIGS. 7 and 8).

A new method to determine binding constants and affinity is the fluorescence proximity sensing using single stranded DNA (96mer) spotted on a chip on DRX2 instrument (Dynamic Biosensors) and complementary DNA coupled to a ligand. In the present study, streptavidin was used as a ligand to capture biotinylated polyacrylamide-coupled Lewis Y or Lewis b. Binding of humanized antibody variant AA9-3-10.1 or competitors' anti-Lewis Y antibodies to the antigen resulted in a fluorescence change. On- and off-rates can be calculated during association and dissociation. AA9-3-10.1 and competitors' anti-LeY antibodies were diluted to 300, 60, and 12 nM in PE140 buffer and applied to the chip-bound antigen. For the experiment with AA9-3-10.1 on Lewis b, 3000, 600 and 120 nM were used, since very low signals were expected. Binding curves were evaluated by mono-exponential global fit (instrument software). Due to a higher sensitivity, faster interactions can be monitored compared to surface plasmon resonance (SPR). This results in binding kinetics different from SPR but more comparable to the "gold standard" method KinExA, measured in a liquid system.

The binding assay showed a strong and highly specific binding of AA9-3-10.1 to Lewis Y. The data confirmed the results of the ELISA assays.

TABLE 4

| antibody | ligand | $k_{ON}$ [M$^{-1}$s$^{-1}$] | $k_{OFF}$ [s$^{-1}$] | $K_D$ [nmol/L] |
|---|---|---|---|---|
| AA9 cIgG1 | Lewis Y | 1.34E+06 | 7.66E−03 | 5.72 |
|  | Lewis b | 7.07E+05 | 3.92E−02 | 55.45 |
| AA9-3-10.1 hIgG1 | Lewis Y | 8.67E+05 | 1.54E−02 | 17.76 |
|  | Lewis b | n.d. | n.d. | n.d. |
| AA9-3-10.1 mIgG1 | Lewis Y | 4.41E+05 | 9.16E−03 | 20.77 |
| BR96 mIgG1 | Lewis Y | 9.46E+05 | 5.41E−02 | 57.19 |
| h3S193 mIgG1 | Lewis Y | n.d. | n.d. | n.d. | n.d.: not determinable

Example 5: Comparison of Tumor Cell Binding of the Humanized Variant AA9-3-10.1 with Known Anti-LeY Antibodies The binding properties of humanized anti-Lewis Y antibody variant AA9-3-10.1, BR96 and 3S193 (all as hIgG1) to the human cancer cell lines Ls-174T, T-47D, H9D8 and Colo-205 were analyzed by flow cytometry. Irrelevant hIgG1 was used as a negative control. Briefly, tumor cells were harvested and incubated with indicated antibodies in serial dilutions at 4° C. in the dark. Afterwards, cells were washed and incubated with a secondary goat anti-hIgG PE-conjugated antibody at 4° C. in the dark. After an additional washing step, cells were stained with DAPI in order to discriminate between live and dead cells and analyzed via flow cytometry.

Humanized anti-Lewis Y antibody variant AA9-3-10.1 showed concentration-dependent binding to Lewis Y-positive cell lines Ls-174T and T-47D and no binding to Lewis Y-negative cell lines H9D8 and Colo-205, whereas the competitor anti-Lewis Y antibodies BR96 and 3S193 showed stronger binding than humanized anti-Lewis Y antibody variant AA9-3-10.1 to all four tumor cell lines (see FIG. 9). Stronger binding of BR96 and 3S193 was most likely due to cross-reactivity. For example, Colo-205 is described to be negative for Lewis Y (Westwood et al., 2005), but positive for Lewis b (Noble et al., 2013).

Example 6: Comparison of Blood Cell Binding of the Humanized Variant AA9-3-10.1 with Known Anti-LeY Antibodies Binding of humanized anti-Lewis Y antibody variant AA9-3-10.1, BR96 and 3S193 (as mIgG1) to leukocytes was determined using flow cytometry. Therefore, whole blood from five healthy volunteers was used. In a first step, red blood cells were lysed and remaining leukocytes were incubated with indicated antibodies [10 μg/ml] at room temperature. Irrelevant mIgG1 was used as a negative control. Afterwards, cells were washed and incubated with a secondary anti-mIgG AF647-conjugated antibody at room temperature. After a washing step, cells were stained with anti-human CD45 PacificBlue-conjugated antibody at room temperature. After an additional washing step, cells were analyzed via flow cytometry. The immune cell subpopulations, granulocytes, monocytes and lymphocytes, were distinguished by their CD45 expression and granularity.

Humanized anti-Lewis Y antibody variant AA9-3-10.1 shows no or only weak binding to leukocyte subsets whereas BR96 binds strongly to granulocytes and 3S193 binds to granulocytes, lymphocytes and monocytes (see FIG. 10). This shows the superior specificity of the humanized anti- Lewis Y antibody variants for tumor cells and their very low cross-reactivity with normal tissue cells.

Example 7: Proliferation Inhibition of Different Tumor Cell Lines Using the Humanized Anti-Lewis Y Antibody Variant AA9-3-10.1 Coupled to a Toxin To demonstrate the efficacy of the humanized anti-Lewis Y antibody variants for killing tumor cells, a proliferation inhibition assay with different tumor cell lines was performed. As cytotoxin, MMAE was coupled to Protein G which binds to the antibody and thereby forms an antibody toxin conjugate.

The cell lines Ls-174T, T-47D, MCF-7 (CSC-enriched), Ovcar-3 and HSC-4 were seeded in culture medium with 5,000 cells/well in a 96-well flat-bottom plate and incubated in presence of humanized anti-Lewis Y antibody variant AA9-3-10.1 (as hIgG1) or irrelevant isotype control in indicated concentrations and ProtG-MMAE for 4 days. Number of viable cells was determined using the commercial CellTiter-Glo Luminescent Cell Viability Assay. Percentage of proliferation was determined relative to a medium only control.

A toxin-coupled humanized anti-Lewis Y antibody variant AA9-3-10.1 is able to inhibit the proliferation of various Lewis Y-expressing tumor cell lines indicating effective internalization of the antibody (see FIG. 11).

Example 8: Immunohistochemical Staining with Humanized Anti-Lewis Y Antibody Variant AA9-3-10.1 of Different Tumor Tissues from Various Cancer Types Binding of humanized anti-Lewis Y antibody variant AA9-3-10.1 to different cancer indications was analyzed by immunohistochemistry. In brief, tissue microarray slides from breast cancer (BRC), non-small cell lung carcinoma (NSCLC), colon carcinoma (CRC), head and neck cancer (HNC), small cell lung carcinoma (SCLC) and ovarian carcinoma (OvCa) were deparaffinized and rehydrated in a descending alcohol series. After antigen retrieval, endogenous peroxidase and unspecific binding was blocked. Binding of humanized anti-Lewis Y antibody variant AA9-3-10.1 as mIgG1 [6.5 µg/ml] was detected with the secondary antibody Envision Flex anti-mouse Ig-HRP and DAB+ staining solution. Finally, slides were counterstained with Mayer's Haematoxylin, mounted and evaluated under the microscope. Binding of humanized anti-Lewis Y antibody variant AA9-3-10.1 is reported using the immunoreactive score (IRS; range 0-12) which is calculated by staining intensity (range 0-3) multiplied by percentage of stained cells (range 0-4).

Humanized anti-Lewis Y antibody variant AA9-3-10.1 stains tumor tissue of breast cancer (BRC), non-small cell lung carcinoma (NSCLC), colon carcinoma (CRC), head and neck cancer (HNC), small cell lung carcinoma (SCLC) and ovarian carcinoma (OVCa) at a high percentage of cases.

TABLE 5

|  | IRS | BRC | NSCLC | CRC | HNC | SCLC | OvCa |
| --- | --- | --- | --- | --- | --- | --- | --- |
| negative | 0 | 1 | 10 | 10 | 22 | 24 | 59 |
| weakly positive | 1-3 | 3 | 12 | 9 | 23 | 18 | 27 |
| moderately positive | 4-8 | 4 | 11 | 11 | 21 | 3 | 14 |
| strongly positive | 9-12 | 2 | 2 | 5 | 3 | 0 | 0 |
| positive cases/total cases |  | 9/10 | 25/35 | 25/35 | 47/69 | 21/45 | 41/100 |
| % positive cases |  | 90% | 71.4% | 71.4% | 68.1% | 46.7% | 41% |

SEQUENCE LISTING

| SEQ ID NO | sequence |
| --- | --- |
| 1 | QVQLVQSGAEVKKPGASVKVSCKASGYTFT DYNID WVRQTPGKGLEWMG YIYPYQGYSDYNQKFKS KATMTVDKSTSTAYMELRSLRSDDTAVYYCAR QLGPGTF WGQGTLVTVS |
| 2 | QVQLVQSGPEVVKPGASVKVSCKASGYTFT DYNID WVRQTPGKGLEWMG YIYPYQGYSDYNQKFKS KATMTVDTSTSTAYMELRSLRSDDTAVYYCAR QLGPGTF WGQGTLVTVS |
| 3 | QVQLVQSGPEVVKPGASVKVSCKASGYTFT DYNID WVRQAPGKGLEWMG YIYPYQGYSDYNQKFKS KATMTVDTSTSTAYMELRSLRSDDTAVYYCAR QLGPGTF WGQGTLVTVS |
| 4 | QVQLVQSGPEVVKPGASVKVSCKASGYTFT DYNID WVRQTPGKGLEWMG YIYPYQGYSDYNQKFKS RVTMTVDKSTSTAYMELRSLRSDDTAVYYCAR QLGPGTF WGQGTLVTVS |
| 5 | QVQLVQSGPEVVKPGASVKVSCKASGYTFT DYNID WVRQAPGQGLEWMG YIYPYQGYSDYNQKFKS KATMTTDTSTSTAYMELRSLRSDDTAVYYCAR QLGPGTF WGQGTLVTVS |
| 6 | QVQLVQSGPEVVKPGASVKVSCKASGYTFT DYNID WVRQTPGKGLEWMG YIYPYQGYSDYNQKFKS KATMTVDKSTSTAYMELRSLRSDDTAVYYCAR QLGPGTF WGQGTLVTVS |
| 7 | QVQLVQSGPEVVKPGASVKVSCKASGYTFT DYNMD WVRQTPGKGLEWMG YIYPYNGYSDYNQKFKS KATMTVDKSTSTAYMELRSLRSDDTAVYYCAR QLGPGTF WGQGTLVTVS |
| 8 | KVQLVQSGPEVVKPGASVKVSCKASGYTFT DYNMD WVKQTPGKSLEWIG YIYPYNGYSDYNQKFKS KATLTVDKSTSTAYMELRSLRSDDTAVYYCAR QLGPGTF WGQGTLVTVS |

SEQUENCE LISTING

| SEQ ID NO | sequence |
|---|---|
| 9 | KVQLVQSGAEVKKPGASVKVSCKASGYTFT DYNMD WVRQAPGQGLEWMG YIYPYNGYSDYNQKFKS KATLTTDTSTSTAYMELRSLRSDDTAVYYCAR QLGPGTF WGQGTLVTVS |
| 10 | XVQLVQSGXEVXKPGASVKVSCKASGYTFT DYNXD WVXQXPGXXLEWMG YIYPYNGYSDYNQKFKS NNTNTNDNSTSTAYMELRSLRSDDTAVYYCAR QLGPGTF WGQGTLVTVS<br>with X1: Q/K, X9: A/P, X12: K/V, X34: I/M, X38: R/K, X40: T/A, N43: K/Q, X44: G/S, X55: Q/N, X67: K/R, X68: A/V, X70: M/L, X72: V/T, X74: K/T |
| 11 | QVQLVQSGXEVXKPGASVKVSCKASGYTFT DYNID WVRQXPGXGLEWMG YIYPYQGYSDYNQKFKS NNTMTNDNSTSTAYMELRSLRSDDTAVYYCAR QLGPGTF WGQGTLVTVS<br>with X9: A/P, X12: K/V, X40: T/A, X43: K/Q, N67: K/R, N68: A/V, N72: V/T, X74: K/T |
| 12 | DYNID |
| 13 | DYNMD |
| 14 | YIYPYQGYSDYNQKFKS |
| 15 | YIYPYNGYSDYNQKFKS |
| 16 | QLGPGTF |
| 17 | DIVMTQTPLSLSVTPGQPASISC KSSQSLLHGNGKTYLN WLLQKPGQSPKLLIY LVSNLESGVPDR FSGSGSGTDFTLKISRVEAEDVGVYYC LQATHFPLT FGQGTKLEIK |
| 18 | DIVMTQTPLSLSVTPGQPTSISC KSSQSLLHGNGKTYLN WLLQKPGQSPKLLIY LVSNLESGVPDR FSGSGSGTDFTLKISRVEAEDLGVYYC LQATHFPLT FGAGAKLEIK |
| 19 | DIVMTQTPLSLSVTPGQPASISC TSSQSLVHSNGNSYLD WYLQKPGQSPQLLIY EVSKRNSGVPDR FSGSGSGTDFTLKISRVEAEDVGVYYC FQRTHLPLT FGQGTKLEIK |
| 20 | DIVLTQTPLSLSVTPGQPASISC TSSQSLVHSNGNSYLD WYLQKPGQSPQLLIY EVSKRNSGVPDR FSGSGSGKDFTLKISRVEAEDVGVYYC FQRTHLPLT FGQGTKLEIK |
| 21 | DIVLTQTPLSLSVTPGQPASISC TSSQSLVHSNGNSYLD WYLQKPGQSLQLLIY EVSKRNSGVPDR FSGSGSGTDFTLKISRVEAEDVGVYYC FQRTHLPLT FGAGTKLEIK |
| 22 | DIVXTQTPLSLSVTPGQPXSISC NSSQSLNHNNGNNYLN WNLQKPGQSNNLLIY NVSNNNSGVPDR FSGSGSGXDFTLKISRVEAEDXGVYYC XQXTHXPLT FGXGXKLEIK<br>with X4: M/L, X19: A/T, N24: K/T, X30: L/V, X32: G/S, X35: K/N, N36: T/S, X39: N/D, X41: L/Y, N49: P/L, X50: K/Q, N55: L/E, X58: N/K, N59: L/R, X60: E/N, X74: T/K, N88: V/L, X94: L/F, N96: A/R, X99: F/L, X105: Q/A, X107: T/A |
| 23 | DIVMTQTPLSLSVTPGQPNSISC KSSQSLLHGNGKTYLN WLLQKPGQSPKLLIY LVSNLES GVPDRFSGSGSGTDFTLKISRVEAEDXGVYYC LQATHFPLT FGXGXKLEIK<br>with X19: A/T, X88: V/L, X105: Q/A, X107: T/A |
| 24 | KSSQSLLHGNGKTYLN |
| 25 | TSSQSLVHSNGNSYLD |
| 26 | LVSNLES |
| 27 | EVSKRNS |
| 28 | LQATHFPLT |
| 29 | FQRTHLPLT |
| 30 | KVKLQQSGPDLVKPGASVKISCKASGYTFT DYNMD WVKQTHAKSLEWIG YIYPYNGYSDYNQKFKS KATLTVDKSSSTAYMELHSLTSEDSAIYYCAR QLGPGTF WGQGTLVTVS |
| 31 | DIVMTQTPLTLSVTIGQPTSISC KSSQSLLHGNGKTYLN WLLQRPGQSPKLLIY LVSNLESGVPDR FSGSGSGTDFTLKISRVEAEDLGVYYC LQATHFPLT FGAGAKLELK |
| 32 | DIVLTQSPLFLHVSLGDQASISC TSSQSLVHSNGNSYLD WHLQKSDQSLQLLIY EVSKRNSGVPDR FSGSGSGKDFTLKISRVEPEDLGIYYC FQRTHLPLT FGAGTKLEIK |

Identification of the Deposited Biological Material

The cell lines DSM ACC 2806, DSM ACC 2807 and DSM ACC 2856 were deposited at the DSMZ—Deutsche Sammlung von Mikroorganismen und Zellkulturen GmbH, Inhoffenstraße 7B, 38124 Braunschweig (DE) by Glycotope GmbH, Robert-Rössle-Str. 10, 13125 Berlin (DE) on the dates indicated in the following table.

| Name of the Cell Line | Accession Number | Depositor | Date of Deposition |
|---|---|---|---|
| NM-H9D8 | DSM ACC 2806 | Glycotope GmbH | Sep. 15, 2006 |
| NM-H9D8-E6 | DSM ACC 2807 | Glycotope GmbH | Oct. 5, 2006 |
| NM-H9D8-E6Q12 | DSM ACC 2856 | Glycotope GmbH | Aug. 8, 2007 |

The invention claimed is:

1. A humanized antibody which is capable of binding to Lewis Y and which comprises a heavy chain variable region and a light chain variable region, wherein;
    (a) the heavy chain variable region comprises the amino acid sequence of SEQ ID NO: 10, and the light chain variable region comprises the amino acid sequence of SEQ ID NO: 22;
    (b) the heavy chain variable region comprises the amino acid sequence of SEQ ID NO: 11 and the light chain variable region comprises the amino acid sequence of SEQ ID NO: 23;
    (c) the heavy chain variable region comprises the amino acid sequence of SEQ ID NO: 1 and the light chain variable region comprises the amino acid sequence of SEQ ID NO: 17;
    (d) the heavy chain variable region comprises the amino acid sequence of SEQ ID NO: 2 and the light chain variable region comprises the amino acid sequence of SEQ ID NO: 17;
    (e) the heavy chain variable region comprises the amino acid sequence of SEQ ID NO: 3 and the light chain variable region comprises the amino acid sequence of SEQ ID NO: 17;
    (f) the heavy chain variable region comprises the amino acid sequence of SEQ ID NO: 4 and the light chain variable region comprises the amino acid sequence of SEQ ID NO: 17;
    (g) the heavy chain variable region comprises the amino acid sequence of SEQ ID NO: 5 and the light chain variable region comprises the amino acid sequence of SEQ ID NO: 17;
    (h) the heavy chain variable region comprises the amino acid sequence of SEQ ID NO: 6 and the light chain variable region comprises the amino acid sequence of SEQ ID NO: 17;
    (i) the heavy chain variable region comprises the amino acid sequence of SEQ ID NO: 7 and the light chain variable region comprises the amino acid sequence of SEQ ID NO: 17;
    (j) the heavy chain variable region comprises the amino acid sequence of SEQ ID NO: 6 and the light chain variable region comprises the amino acid sequence of SEQ ID NO: 18; or
    (k) the heavy chain variable region comprises the amino acid sequence of SEQ ID NO: 8 and the light chain variable region comprises the amino acid sequence of SEQ ID NO: 18.

2. The antibody according to claim 1, wherein the antibody comprises:
    (a) complementarity determining regions CDR-H1 having the amino acid sequence of SEQ ID NO: 12, CDR-H2 having the amino acid sequence of SEQ ID NO: 14, and CDR-H3 having the amino acid sequence of SEQ ID NO: 16, CDR-L1 having the amino acid sequence of SEQ ID NO: 24, CDR-L2 having the amino acid sequence of SEQ ID NO: 26, and CDR-L3 having the amino acid sequence of SEQ ID NO: 28; or
    (b) complementarity determining region CDR-H1 having the amino acid sequence of SEQ ID NO: 13, CDR-H2 having the amino acid sequence of SEQ ID NO: 15, CDR-H3 having the amino acid sequence of SEQ ID NO: 16, CDR-L1 having the amino acid sequence of SEQ ID NO: 25, CDR-L2 having the amino acid sequence of SEQ ID NO: 27, and CDR-L3 having the amino acid sequence of SEQ ID NO: 29.

3. The antibody according to claim 1, wherein the heavy chain variable region comprises the amino acid sequence of SEQ ID NO: 11 and the light chain variable region comprises the amino acid sequence of SEQ ID NO: 23.

4. The antibody according to claim 1, wherein the heavy chain variable region comprises the amino acid sequence of SEQ ID NO: 1 and the light chain variable region comprises the amino acid sequence of SEQ ID NO: 17.

5. The antibody according to claim 1 further comprising an Fc region.

6. The antibody according to claim 5, being wherein said antibody is an IgG1-type, IgG2-type, IgG3-type or IgG4-type antibody.

7. The antibody according to claim 1, being capable of specifically binding Lewis Y, but not Lewis b.

8. A nucleic acid encoding the antibody according to claim 1.

9. An expression cassette or vector comprising the nucleic acid according to claim 8 and a promoter operatively connected with said nucleic acid.

10. A host cell comprising the nucleic acid according to claim 8.

11. A conjugate comprising the antibody according to claim 1 conjugated to a further agent.

12. The conjugate according to claim 11, wherein the further agent is a cytotoxic agent, tumor-specific antibody or immune checkpoint blocking or activating antibody.

13. The conjugate according to claim 11, being a chimeric antigen receptor.

14. A composition comprising the antibody according to claim 1.

15. The composition according to claim 14 being a pharmaceutical composition which preferably further comprises one or more components selected from the group consisting of solvents, diluents and excipients.

16. A method of treating a patient having cancer, comprising administering to the patient the antibody of claim 1.

17. The method according to claim 16, wherein the cancer is selected from the group consisting of lung cancer, colon cancer, colorectal cancer, breast cancer, ovarian cancer, gastric cancer, leukemia, lymphoma, multiple myeloma, head and neck cancer, pancreatic cancer, liver cancer, prostate cancer and bladder cancer.

18. A method of treating a patient having cancer, comprising administering to the patient the conjugate of claim 11.

* * * * *

```
                               SEQUENCE LISTING

<160> NUMBER OF SEQ ID NOS: 32

<210> SEQ ID NO 1
<211> LENGTH: 115
<212> TYPE: PRT
<213> ORGANISM: Artificial Sequence
<220> FEATURE:
<223> OTHER INFORMATION: heavy chain variable region

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Asn Ile Asp Trp Val Arg Gln Thr Pro Gly Lys Gly Leu Glu Trp Met
            35                  40                  45

Gly Tyr Ile Tyr Pro Tyr Gln Gly Tyr Ser Asp Tyr Asn Gln Lys Phe
        50                  55                  60

Lys Ser Lys Ala Thr Met Thr Val Asp Lys Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gln Leu Gly Pro Gly Thr Phe Trp Gly Gln Gly Thr Leu Val
                100                 105                 110

Thr Val Ser
        115

<210> SEQ ID NO 2
<211> LENGTH: 115
<212> TYPE: PRT
<213> ORGANISM: Artificial Sequence
<220> FEATURE:
<223> OTHER INFORMATION: heavy chain variable region

<400> SEQUENCE: 2

Gln Val Gln Leu Val Gln Ser Gly Pro Glu Val Val Lys Pro Gly Ala
1               5                   10                  15

Ser Val Lys Val Ser Cys Lys Ala Ser Gly Tyr Thr Phe Thr Asp Tyr
                20                  25                  30

Asn Ile Asp Trp Val Arg Gln Thr Pro Gly Lys Gly Leu Glu Trp Met
            35                  40                  45

Gly Tyr Ile Tyr Pro Tyr Gln Gly Tyr Ser Asp Tyr Asn Gln Lys Phe
        50                  55                  60

Lys Ser Lys Ala Thr Met Thr Val Asp Thr Ser Thr Ser Thr Ala Tyr
```

```
                65                  70                  75                  80
Met Glu Leu Arg Ser Leu Arg Ser Asp Asp Thr Ala Val Tyr Tyr Cys
                    85                  90                  95

Ala Arg Gln Leu Gly Pro Gly Thr Phe Trp Gly Gln Gly Thr Leu Val
                100                 105                 110

Thr Val Ser
        115

<210> SEQ ID NO 3
<211> LENGTH: 115
<212> TYPE: PRT
<213> ORGANISM: Artificial Sequence
<220> FEATURE:
<223> OTHER INFORMATION: heavy chain variable region

<400> SEQUENCE: 3

Gln Val Gln Leu Val Gln Ser Gly Pro Glu Val Val Lys Pro Gly Ala
1               5                   10                  15

Ser Val Lys Val Ser Cys Lys Ala Ser Gly Tyr Thr Phe Thr Asp Tyr
                20                  25                  30

Asn Ile Asp Trp Val Arg Gln Ala Pro Gly Lys Gly Leu Glu Trp Met
            35                  40                  45

Gly Tyr Ile Tyr Pro Tyr Gln Gly Tyr Ser Asp Tyr Asn Gln Lys Phe
        50                  55                  60

Lys Ser Lys Ala Thr Met Thr Val Asp Thr Ser Thr Ser Thr Ala Tyr
65                  70                  75                  80

Met Glu Leu Arg Ser Leu Arg Ser Asp Asp Thr Ala Val Tyr Tyr Cys
                    85                  90                  95

Ala Arg Gln Leu Gly Pro Gly Thr Phe Trp Gly Gln Gly Thr Leu Val
                100                 105                 110

Thr Val Ser
        115

<210> SEQ ID NO 4
<211> LENGTH: 115
<212> TYPE: PRT
<213> ORGANISM: Artificial Sequence
<220> FEATURE:
<223> OTHER INFORMATION: heavy chain variable region

<400> SEQUENCE: 4

Gln Val Gln Leu Val Gln Ser Gly Pro Glu Val Val Lys Pro Gly Ala
1               5                   10                  15

Ser Val Lys Val Ser Cys Lys Ala Ser Gly Tyr Thr Phe Thr Asp Tyr
                20                  25                  30

Asn Ile Asp Trp Val Arg Gln Thr Pro Gly Lys Gly Leu Glu Trp Met
            35                  40                  45

Gly Tyr Ile Tyr Pro Tyr Gln Gly Tyr Ser Asp Tyr Asn Gln Lys Phe
        50                  55                  60

Lys Ser Arg Val Thr Met Thr Val Asp Lys Ser Thr Ser Thr Ala Tyr
65                  70                  75                  80

Met Glu Leu Arg Ser Leu Arg Ser Asp Asp Thr Ala Val Tyr Tyr Cys
                    85                  90                  95

Ala Arg Gln Leu Gly Pro Gly Thr Phe Trp Gly Gln Gly Thr Leu Val
                100                 105                 110

Thr Val Ser
        115
```

```
<210> SEQ ID NO 5
<211> LENGTH: 115
<212> TYPE: PRT
<213> ORGANISM: Artificial Sequence
<220> FEATURE:
<223> OTHER INFORMATION: heavy chain variable region

<400> SEQUENCE: 5

Gln Val Gln Leu Val Gln Ser Gly Pro Glu Val Val Lys Pro Gly Ala
1               5                   10                  15

Ser Val Lys Val Ser Cys Lys Ala Ser Gly Tyr Thr Phe Thr Asp Tyr
            20                  25                  30

Asn Ile Asp Trp Val Arg Gln Ala Pro Gly Gln Gly Leu Glu Trp Met
        35                  40                  45

Gly Tyr Ile Tyr Pro Tyr Gln Gly Tyr Ser Asp Tyr Asn Gln Lys Phe
    50                  55                  60

Lys Ser Lys Ala Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gln Leu Gly Pro Gly Thr Phe Trp Gly Gln Gly Thr Leu Val
            100                 105                 110

Thr Val Ser
        115

<210> SEQ ID NO 6
<211> LENGTH: 115
<212> TYPE: PRT
<213> ORGANISM: Artificial Sequence
<220> FEATURE:
<223> OTHER INFORMATION: heavy chain variable region

<400> SEQUENCE: 6

Gln Val Gln Leu Val Gln Ser Gly Pro Glu Val Val Lys Pro Gly Ala
1               5                   10                  15

Ser Val Lys Val Ser Cys Lys Ala Ser Gly Tyr Thr Phe Thr Asp Tyr
            20                  25                  30

Asn Ile Asp Trp Val Arg Gln Thr Pro Gly Lys Gly Leu Glu Trp Met
        35                  40                  45

Gly Tyr Ile Tyr Pro Tyr Gln Gly Tyr Ser Asp Tyr Asn Gln Lys Phe
    50                  55                  60

Lys Ser Lys Ala Thr Met Thr Val Asp Lys Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gln Leu Gly Pro Gly Thr Phe Trp Gly Gln Gly Thr Leu Val
            100                 105                 110

Thr Val Ser
        115

<210> SEQ ID NO 7
<211> LENGTH: 115
<212> TYPE: PRT
<213> ORGANISM: Artificial Sequence
<220> FEATURE:
<223> OTHER INFORMATION: heavy chain variable region

<400> SEQUENCE: 7

Gln Val Gln Leu Val Gln Ser Gly Pro Glu Val Val Lys Pro Gly Ala
```

-continued

```
                 1               5                  10                  15
               Ser Val Lys Val Ser Cys Lys Ala Ser Gly Tyr Thr Phe Thr Asp Tyr
                               20                  25                  30

Asn Met Asp Trp Val Arg Gln Thr Pro Gly Lys Gly Leu Glu Trp Met
                           35                  40                  45

Gly Tyr Ile Tyr Pro Tyr Asn Gly Tyr Ser Asp Tyr Asn Gln Lys Phe
                       50                  55                  60

Lys Ser Lys Ala Thr Met Thr Val Asp Lys Ser Thr Ser Thr Ala Tyr
                65                  70                  75                  80

Met Glu Leu Arg Ser Leu Arg Ser Asp Asp Thr Ala Val Tyr Tyr Cys
                               85                  90                  95

Ala Arg Gln Leu Gly Pro Gly Thr Phe Trp Gly Gln Gly Thr Leu Val
                               100                 105                 110

Thr Val Ser
                       115
```

<210> SEQ ID NO 8
<211> LENGTH: 115
<212> TYPE: PRT
<213> ORGANISM: Artificial Sequence
<220> FEATURE:
<223> OTHER INFORMATION: heavy chain variable region

<400> SEQUENCE: 8

```
               Lys Val Gln Leu Val Gln Ser Gly Pro Glu Val Val Lys Pro Gly Ala
                1               5                  10                  15

Ser Val Lys Val Ser Cys Lys Ala Ser Gly Tyr Thr Phe Thr Asp Tyr
                               20                  25                  30

Asn Met Asp Trp Val Lys Gln Thr Pro Gly Lys Ser Leu Glu Trp Ile
                           35                  40                  45

Gly Tyr Ile Tyr Pro Tyr Asn Gly Tyr Ser Asp Tyr Asn Gln Lys Phe
                       50                  55                  60

Lys Ser Lys Ala Thr Leu Thr Val Asp Lys Ser Thr Ser Thr Ala Tyr
                65                  70                  75                  80

Met Glu Leu Arg Ser Leu Arg Ser Asp Asp Thr Ala Val Tyr Tyr Cys
                               85                  90                  95

Ala Arg Gln Leu Gly Pro Gly Thr Phe Trp Gly Gln Gly Thr Leu Val
                               100                 105                 110

Thr Val Ser
                       115
```

<210> SEQ ID NO 9
<211> LENGTH: 115
<212> TYPE: PRT
<213> ORGANISM: Artificial Sequence
<220> FEATURE:
<223> OTHER INFORMATION: heavy chain variable region

<400> SEQUENCE: 9

```
               Lys Val Gln Leu Val Gln Ser Gly Ala Glu Val Lys Lys Pro Gly Ala
                1               5                  10                  15

Ser Val Lys Val Ser Cys Lys Ala Ser Gly Tyr Thr Phe Thr Asp Tyr
                               20                  25                  30

Asn Met Asp Trp Val Arg Gln Ala Pro Gly Gln Gly Leu Glu Trp Met
                           35                  40                  45

Gly Tyr Ile Tyr Pro Tyr Asn Gly Tyr Ser Asp Tyr Asn Gln Lys Phe
                       50                  55                  60
```

-continued

```
Lys Ser Lys Ala Thr Leu Thr Thr Asp Thr Ser Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Gln Leu Gly Pro Gly Thr Phe Trp Gly Gln Gly Thr Leu Val
            100                 105                 110

Thr Val Ser
        115

<210> SEQ ID NO 10
<211> LENGTH: 115
<212> TYPE: PRT
<213> ORGANISM: Artificial Sequence
<220> FEATURE:
<223> OTHER INFORMATION: heavy chain variable region
<220> FEATURE:
<221> NAME/KEY: VARIANT
<222> LOCATION: 1
<223> OTHER INFORMATION: Xaa is Gln or Lys
<220> FEATURE:
<221> NAME/KEY: VARIANT
<222> LOCATION: 9
<223> OTHER INFORMATION: Xaa is Ala or Pro
<220> FEATURE:
<221> NAME/KEY: VARIANT
<222> LOCATION: 12
<223> OTHER INFORMATION: Xaa is Lys or Val
<220> FEATURE:
<221> NAME/KEY: VARIANT
<222> LOCATION: 34
<223> OTHER INFORMATION: Xaa is Ile or Met
<220> FEATURE:
<221> NAME/KEY: VARIANT
<222> LOCATION: 38
<223> OTHER INFORMATION: Xaa is Arg or Lys
<220> FEATURE:
<221> NAME/KEY: VARIANT
<222> LOCATION: 40
<223> OTHER INFORMATION: Xaa is Thr or Ala
<220> FEATURE:
<221> NAME/KEY: VARIANT
<222> LOCATION: 43
<223> OTHER INFORMATION: Xaa is Lys or Gln
<220> FEATURE:
<221> NAME/KEY: VARIANT
<222> LOCATION: 44
<223> OTHER INFORMATION: Xaa is Gly or Ser
<220> FEATURE:
<221> NAME/KEY: VARIANT
<222> LOCATION: 55
<223> OTHER INFORMATION: Xaa is Gln or Asn
<220> FEATURE:
<221> NAME/KEY: VARIANT
<222> LOCATION: 67
<223> OTHER INFORMATION: Xaa is Lys or Arg
<220> FEATURE:
<221> NAME/KEY: VARIANT
<222> LOCATION: 68
<223> OTHER INFORMATION: Xaa is Ala or Val
<220> FEATURE:
<221> NAME/KEY: VARIANT
<222> LOCATION: 70
<223> OTHER INFORMATION: Xaa is Met or Leu
<220> FEATURE:
<221> NAME/KEY: VARIANT
<222> LOCATION: 72
<223> OTHER INFORMATION: Xaa is Val or Thr
<220> FEATURE:
<221> NAME/KEY: VARIANT
<222> LOCATION: 74
<223> OTHER INFORMATION: Xaa is Lys or Thr

<400> SEQUENCE: 10

Xaa Val Gln Leu Val Gln Ser Gly Xaa Glu Val Xaa Lys Pro Gly Ala
```

-continued

```
                1               5                   10                  15
            Ser Val Lys Val Ser Cys Lys Ala Ser Gly Tyr Thr Phe Thr Asp Tyr
                            20                  25                  30

Asn Xaa Asp Trp Val Xaa Gln Xaa Pro Gly Xaa Xaa Leu Glu Trp Met
                        35                  40                  45

Gly Tyr Ile Tyr Pro Tyr Xaa Gly Tyr Ser Asp Tyr Asn Gln Lys Phe
                    50                  55                  60

Lys Ser Xaa Xaa Thr Xaa Thr Xaa Asp Xaa Ser Thr Ser Thr Ala Tyr
                65                  70                  75                  80

Met Glu Leu Arg Ser Leu Arg Ser Asp Asp Thr Ala Val Tyr Tyr Cys
                            85                  90                  95

Ala Arg Gln Leu Gly Pro Gly Thr Phe Trp Gly Gln Gly Thr Leu Val
                        100                 105                 110

Thr Val Ser
                    115

<210> SEQ ID NO 11
<211> LENGTH: 115
<212> TYPE: PRT
<213> ORGANISM: Artificial Sequence
<220> FEATURE:
<223> OTHER INFORMATION: heavy chain variable region
<220> FEATURE:
<221> NAME/KEY: VARIANT
<222> LOCATION: 9
<223> OTHER INFORMATION: Xaa is Ala or Pro
<220> FEATURE:
<221> NAME/KEY: VARIANT
<222> LOCATION: 12
<223> OTHER INFORMATION: Xaa is Lys or Val
<220> FEATURE:
<221> NAME/KEY: VARIANT
<222> LOCATION: 40
<223> OTHER INFORMATION: Xaa is Thr or Ala
<220> FEATURE:
<221> NAME/KEY: VARIANT
<222> LOCATION: 43
<223> OTHER INFORMATION: Xaa is Lys or Gln
<220> FEATURE:
<221> NAME/KEY: VARIANT
<222> LOCATION: 67
<223> OTHER INFORMATION: Xaa is Lys or Arg
<220> FEATURE:
<221> NAME/KEY: VARIANT
<222> LOCATION: 68
<223> OTHER INFORMATION: Xaa is Ala or Val
<220> FEATURE:
<221> NAME/KEY: VARIANT
<222> LOCATION: 72
<223> OTHER INFORMATION: Xaa is Val or Thr
<220> FEATURE:
<221> NAME/KEY: VARIANT
<222> LOCATION: 74
<223> OTHER INFORMATION: Xaa is Lys or Thr

<400> SEQUENCE: 11

Gln Val Gln Leu Val Gln Ser Gly Xaa Glu Val Xaa Lys Pro Gly Ala
            1               5                   10                  15

Ser Val Lys Val Ser Cys Lys Ala Ser Gly Tyr Thr Phe Thr Asp Tyr
                            20                  25                  30

Asn Ile Asp Trp Val Arg Gln Xaa Pro Gly Xaa Gly Leu Glu Trp Met
                        35                  40                  45

Gly Tyr Ile Tyr Pro Tyr Gln Gly Tyr Ser Asp Tyr Asn Gln Lys Phe
                    50                  55                  60

Lys Ser Xaa Xaa Thr Met Thr Xaa Asp Xaa Ser Thr Ser Thr Ala Tyr
                65                  70                  75                  80
```

```
Met Glu Leu Arg Ser Leu Arg Ser Asp Asp Thr Ala Val Tyr Tyr Cys
                85                  90                  95

Ala Arg Gln Leu Gly Pro Gly Thr Phe Trp Gly Gln Gly Thr Leu Val
            100                 105                 110

Thr Val Ser
        115

<210> SEQ ID NO 12
<211> LENGTH: 5
<212> TYPE: PRT
<213> ORGANISM: Artificial Sequence
<220> FEATURE:
<223> OTHER INFORMATION: CDR-H1

<400> SEQUENCE: 12

Asp Tyr Asn Ile Asp
1               5

<210> SEQ ID NO 13
<211> LENGTH: 5
<212> TYPE: PRT
<213> ORGANISM: Artificial Sequence
<220> FEATURE:
<223> OTHER INFORMATION: CDR-H1

<400> SEQUENCE: 13

Asp Tyr Asn Met Asp
1               5

<210> SEQ ID NO 14
<211> LENGTH: 17
<212> TYPE: PRT
<213> ORGANISM: Artificial Sequence
<220> FEATURE:
<223> OTHER INFORMATION: CDR-H2

<400> SEQUENCE: 14

Tyr Ile Tyr Pro Tyr Gln Gly Tyr Ser Asp Tyr Asn Gln Lys Phe Lys
1               5                   10                  15

Ser

<210> SEQ ID NO 15
<211> LENGTH: 17
<212> TYPE: PRT
<213> ORGANISM: Artificial Sequence
<220> FEATURE:
<223> OTHER INFORMATION: CDR-H2

<400> SEQUENCE: 15

Tyr Ile Tyr Pro Tyr Asn Gly Tyr Ser Asp Tyr Asn Gln Lys Phe Lys
1               5                   10                  15

Ser

<210> SEQ ID NO 16
<211> LENGTH: 7
<212> TYPE: PRT
<213> ORGANISM: Artificial Sequence
<220> FEATURE:
<223> OTHER INFORMATION: CDR-H3

<400> SEQUENCE: 16

Gln Leu Gly Pro Gly Thr Phe
1               5
```

```
<210> SEQ ID NO 17
<211> LENGTH: 112
<212> TYPE: PRT
<213> ORGANISM: Artificial Sequence
<220> FEATURE:
<223> OTHER INFORMATION: light chain variable region

<400> SEQUENCE: 17

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Gly
            20                  25                  30

Asn Gly Lys Thr Tyr Leu Asn Trp Leu Leu Gln Lys Pro Gly Gln Ser
        35                  40                  45

Pro Lys Leu Leu Ile Tyr Leu Val Ser Asn Leu Glu Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Ala
                85                  90                  95

Thr His Phe Pro Leu Thr Phe Gly Gln Gly Thr Lys Leu Glu Ile Lys
            100                 105                 110

<210> SEQ ID NO 18
<211> LENGTH: 112
<212> TYPE: PRT
<213> ORGANISM: Artificial Sequence
<220> FEATURE:
<223> OTHER INFORMATION: light chain variable region

<400> SEQUENCE: 18

Asp Ile Val Met Thr Gln Thr Pro Leu Ser Leu Ser Val Thr Pro Gly
1               5                   10                  15

Gln Pro Thr Ser Ile Ser Cys Lys Ser Ser Gln Ser Leu Leu His Gly
            20                  25                  30

Asn Gly Lys Thr Tyr Leu Asn Trp Leu Leu Gln Lys Pro Gly Gln Ser
        35                  40                  45

Pro Lys Leu Leu Ile Tyr Leu Val Ser Asn Leu Glu Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Leu Gln Ala
                85                  90                  95

Thr His Phe Pro Leu Thr Phe Gly Ala Gly Ala Lys Leu Glu Ile Lys
            100                 105                 110

<210> SEQ ID NO 19
<211> LENGTH: 112
<212> TYPE: PRT
<213> ORGANISM: Artificial Sequence
<220> FEATURE:
<223> OTHER INFORMATION: light chain variable region

<400> SEQUENCE: 19

Asp Ile Val Met Thr Gln Thr Pro Leu Ser Leu Ser Val Thr Pro Gly
1               5                   10                  15

Gln Pro Ala Ser Ile Ser Cys Thr Ser Ser Gln Ser Leu Val His Ser
            20                  25                  30

Asn Gly Asn Ser Tyr Leu Asp Trp Tyr Leu Gln Lys Pro Gly Gln Ser
```

```
                35                  40                  45
Pro Gln Leu Leu Ile Tyr Glu Val Ser Lys Arg Asn Ser Gly Val Pro
    50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Arg
                 85                  90                  95

Thr His Leu Pro Leu Thr Phe Gly Gln Gly Thr Lys Leu Glu Ile Lys
            100                 105                 110

<210> SEQ ID NO 20
<211> LENGTH: 112
<212> TYPE: PRT
<213> ORGANISM: Artificial Sequence
<220> FEATURE:
<223> OTHER INFORMATION: light chain variable region

<400> SEQUENCE: 20

Asp Ile Val Leu Thr Gln Thr Pro Leu Ser Leu Ser Val Thr Pro Gly
  1               5                  10                  15

Gln Pro Ala Ser Ile Ser Cys Thr Ser Ser Gln Ser Leu Val His Ser
                 20                  25                  30

Asn Gly Asn Ser Tyr Leu Asp Trp Tyr Leu Gln Lys Pro Gly Gln Ser
            35                  40                  45

Pro Gln Leu Leu Ile Tyr Glu Val Ser Lys Arg Asn Ser Gly Val Pro
    50                  55                  60

Asp Arg Phe Ser Gly Ser Gly Ser Gly Lys Asp Phe Thr Leu Lys Ile
 65                  70                  75                  80

Ser Arg Val Glu Ala Glu Asp Val Gly Val Tyr Tyr Cys Phe Gln Arg
                 85                  90                  95

Thr His Leu Pro Leu Thr Phe Gly Gln Gly Thr Lys Leu Glu Ile Lys
            100                 105                 110

<210> SEQ ID NO 21
<211> LENGTH: 112
<212> TYPE: PRT
<213> ORGANISM: Artificial Sequence
<220> FEATURE:
<223> OTHER INFORMATION: light chain variable region

<400> SEQUENCE: 21

Asp Ile Val Leu Thr Gln Thr Pro Leu Ser Leu Ser Val Thr Pro Gly
  1               5                  10                  15

Gln Pro Ala Ser Ile Ser Cys Thr Ser Ser Gln Ser Leu Val His Ser
                 20                  25                  30

Asn Gly Asn Ser Tyr Leu Asp Trp Tyr Leu Gln Lys Pro Gly Gln Ser
            35                  40                  45

Leu Gln Leu Leu Ile Tyr Glu Val Ser Lys Arg Asn Ser Gly Val Pro
    50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Arg
                 85                  90                  95

Thr His Leu Pro Leu Thr Phe Gly Ala Gly Thr Lys Leu Glu Ile Lys
            100                 105                 110

<210> SEQ ID NO 22
<211> LENGTH: 112
```

```
<212> TYPE: PRT
<213> ORGANISM: Artificial Sequence
<220> FEATURE:
<223> OTHER INFORMATION: light chain variable region
<220> FEATURE:
<221> NAME/KEY: VARIANT
<222> LOCATION: 4
<223> OTHER INFORMATION: Xaa is Met or Leu
<220> FEATURE:
<221> NAME/KEY: VARIANT
<222> LOCATION: 19
<223> OTHER INFORMATION: Xaa is Ala or Thr
<220> FEATURE:
<221> NAME/KEY: VARIANT
<222> LOCATION: 24
<223> OTHER INFORMATION: Xaa is Lys or Thr
<220> FEATURE:
<221> NAME/KEY: VARIANT
<222> LOCATION: 30
<223> OTHER INFORMATION: Xaa is Leu or Val
<220> FEATURE:
<221> NAME/KEY: VARIANT
<222> LOCATION: 32
<223> OTHER INFORMATION: Xaa is Gly or Ser
<220> FEATURE:
<221> NAME/KEY: VARIANT
<222> LOCATION: 35
<223> OTHER INFORMATION: Xaa is Lys or Asn
<220> FEATURE:
<221> NAME/KEY: VARIANT
<222> LOCATION: 36
<223> OTHER INFORMATION: Xaa is Thr or Ser
<220> FEATURE:
<221> NAME/KEY: VARIANT
<222> LOCATION: 39
<223> OTHER INFORMATION: Xaa is Asn or Asp
<220> FEATURE:
<221> NAME/KEY: VARIANT
<222> LOCATION: 41
<223> OTHER INFORMATION: Xaa is Leu or Tyr
<220> FEATURE:
<221> NAME/KEY: VARIANT
<222> LOCATION: 49
<223> OTHER INFORMATION: Xaa is Pro or Leu
<220> FEATURE:
<221> NAME/KEY: VARIANT
<222> LOCATION: 50
<223> OTHER INFORMATION: Xaa is Lys or Gln
<220> FEATURE:
<221> NAME/KEY: VARIANT
<222> LOCATION: 55
<223> OTHER INFORMATION: Xaa is Leu or Glu
<220> FEATURE:
<221> NAME/KEY: VARIANT
<222> LOCATION: 58
<223> OTHER INFORMATION: Xaa is Asn or Lys
<220> FEATURE:
<221> NAME/KEY: VARIANT
<222> LOCATION: 59
<223> OTHER INFORMATION: Xaa is Leu or Arg
<220> FEATURE:
<221> NAME/KEY: VARIANT
<222> LOCATION: 60
<223> OTHER INFORMATION: Xaa is Glu or Asn
<220> FEATURE:
<221> NAME/KEY: VARIANT
<222> LOCATION: 74
<223> OTHER INFORMATION: Xaa is Thr or Lys
<220> FEATURE:
<221> NAME/KEY: VARIANT
<222> LOCATION: 88
<223> OTHER INFORMATION: Xaa is Val or Leu
<220> FEATURE:
<221> NAME/KEY: VARIANT
<222> LOCATION: 94
<223> OTHER INFORMATION: Xaa is Leu or Phe
<220> FEATURE:
<221> NAME/KEY: VARIANT
<222> LOCATION: 96
```

```
<223> OTHER INFORMATION: Xaa is Ala or Arg
<220> FEATURE:
<221> NAME/KEY: VARIANT
<222> LOCATION: 99
<223> OTHER INFORMATION: Xaa is Phe or Leu
<220> FEATURE:
<221> NAME/KEY: VARIANT
<222> LOCATION: 105
<223> OTHER INFORMATION: Xaa is Gln or Ala
<220> FEATURE:
<221> NAME/KEY: VARIANT
<222> LOCATION: 107
<223> OTHER INFORMATION: Xaa is Thr or Ala

<400> SEQUENCE: 22

Asp Ile Val Xaa Thr Gln Thr Pro Leu Ser Leu Ser Val Thr Pro Gly
 1               5                  10                  15

Gln Pro Xaa Ser Ile Ser Cys Xaa Ser Ser Gln Ser Leu Xaa His Xaa
            20                  25                  30

Asn Gly Xaa Xaa Tyr Leu Xaa Trp Xaa Leu Gln Lys Pro Gly Gln Ser
        35                  40                  45

Xaa Xaa Leu Leu Ile Tyr Xaa Val Ser Xaa Xaa Xaa Ser Gly Val Pro
    50                  55                  60

Asp Arg Phe Ser Gly Ser Gly Ser Gly Xaa Asp Phe Thr Leu Lys Ile
65                  70                  75                  80

Ser Arg Val Glu Ala Glu Asp Xaa Gly Val Tyr Tyr Cys Xaa Gln Xaa
                85                  90                  95

Thr His Xaa Pro Leu Thr Phe Gly Xaa Gly Xaa Lys Leu Glu Ile Lys
            100                 105                 110

<210> SEQ ID NO 23
<211> LENGTH: 112
<212> TYPE: PRT
<213> ORGANISM: Artificial Sequence
<220> FEATURE:
<223> OTHER INFORMATION: light chain variable region
<220> FEATURE:
<221> NAME/KEY: VARIANT
<222> LOCATION: 19
<223> OTHER INFORMATION: Xaa is Ala or Thr
<220> FEATURE:
<221> NAME/KEY: VARIANT
<222> LOCATION: 88
<223> OTHER INFORMATION: Xaa is Val or Leu
<220> FEATURE:
<221> NAME/KEY: VARIANT
<222> LOCATION: 105
<223> OTHER INFORMATION: Xaa is Gln or Ala
<220> FEATURE:
<221> NAME/KEY: VARIANT
<222> LOCATION: 107
<223> OTHER INFORMATION: Xaa is Thr or Ala

<400> SEQUENCE: 23

Asp Ile Val Met Thr Gln Thr Pro Leu Ser Leu Ser Val Thr Pro Gly
 1               5                  10                  15

Gln Pro Xaa Ser Ile Ser Cys Lys Ser Ser Gln Ser Leu Leu His Gly
            20                  25                  30

Asn Gly Lys Thr Tyr Leu Asn Trp Leu Leu Gln Lys Pro Gly Gln Ser
        35                  40                  45

Pro Lys Leu Leu Ile Tyr Leu Val Ser Asn Leu Glu Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Xaa Gly Val Tyr Tyr Cys Leu Gln Ala
                85                  90                  95
```

```
                        85                  90                  95
Thr His Phe Pro Leu Thr Phe Gly Xaa Gly Xaa Lys Leu Glu Ile Lys
            100                 105                 110
```

<210> SEQ ID NO 24
<211> LENGTH: 16
<212> TYPE: PRT
<213> ORGANISM: Artificial Sequence
<220> FEATURE:
<223> OTHER INFORMATION: CDR-L1

<400> SEQUENCE: 24

```
Lys Ser Ser Gln Ser Leu Leu His Gly Asn Gly Lys Thr Tyr Leu Asn
1               5                   10                  15
```

<210> SEQ ID NO 25
<211> LENGTH: 16
<212> TYPE: PRT
<213> ORGANISM: Artificial Sequence
<220> FEATURE:
<223> OTHER INFORMATION: CDR-L1

<400> SEQUENCE: 25

```
Thr Ser Ser Gln Ser Leu Val His Ser Asn Gly Asn Ser Tyr Leu Asp
1               5                   10                  15
```

<210> SEQ ID NO 26
<211> LENGTH: 7
<212> TYPE: PRT
<213> ORGANISM: Artificial Sequence
<220> FEATURE:
<223> OTHER INFORMATION: CDR-L2

<400> SEQUENCE: 26

```
Leu Val Ser Asn Leu Glu Ser
1               5
```

<210> SEQ ID NO 27
<211> LENGTH: 7
<212> TYPE: PRT
<213> ORGANISM: Artificial Sequence
<220> FEATURE:
<223> OTHER INFORMATION: CDR-L2

<400> SEQUENCE: 27

```
Glu Val Ser Lys Arg Asn Ser
1               5
```

<210> SEQ ID NO 28
<211> LENGTH: 9
<212> TYPE: PRT
<213> ORGANISM: Artificial Sequence
<220> FEATURE:
<223> OTHER INFORMATION: CDR-L3

<400> SEQUENCE: 28

```
Leu Gln Ala Thr His Phe Pro Leu Thr
1               5
```

<210> SEQ ID NO 29
<211> LENGTH: 9
<212> TYPE: PRT
<213> ORGANISM: Artificial Sequence
<220> FEATURE:
<223> OTHER INFORMATION: CDR-L3

<400> SEQUENCE: 29

Phe Gln Arg Thr His Leu Pro Leu Thr
1               5

<210> SEQ ID NO 30
<211> LENGTH: 115
<212> TYPE: PRT
<213> ORGANISM: Artificial Sequence
<220> FEATURE:
<223> OTHER INFORMATION: heavy chain variable region

<400> SEQUENCE: 30

Lys Val Lys Leu Gln Gln Ser Gly Pro Asp Leu Val Lys Pro Gly Ala
1               5                   10                  15

Ser Val Lys Ile Ser Cys Lys Ala Ser Gly Tyr Thr Phe Thr Asp Tyr
                20                  25                  30

Asn Met Asp Trp Val Lys Gln Thr His Ala Lys Ser Leu Glu Trp Ile
            35                  40                  45

Gly Tyr Ile Tyr Pro Tyr Asn Gly Tyr Ser Asp Tyr Asn Gln Lys Phe
        50                  55                  60

Lys Ser Lys Ala Thr Leu Thr Val Asp Lys Ser Ser Ser Thr Ala Tyr
65                  70                  75                  80

Met Glu Leu His Ser Leu Thr Ser Glu Asp Ser Ala Ile Tyr Tyr Cys
                85                  90                  95

Ala Arg Gln Leu Gly Pro Gly Thr Phe Trp Gly Gln Gly Thr Leu Val
                100                 105                 110

Thr Val Ser
        115

<210> SEQ ID NO 31
<211> LENGTH: 112
<212> TYPE: PRT
<213> ORGANISM: Artificial Sequence
<220> FEATURE:
<223> OTHER INFORMATION: light chain variable region

<400> SEQUENCE: 31

Asp Ile Val Met Thr Gln Thr Pro Leu Thr Leu Ser Val Thr Ile Gly
1               5                   10                  15

Gln Pro Thr Ser Ile Ser Cys Lys Ser Ser Gln Ser Leu Leu His Gly
                20                  25                  30

Asn Gly Lys Thr Tyr Leu Asn Trp Leu Leu Gln Arg Pro Gly Gln Ser
            35                  40                  45

Pro Lys Leu Leu Ile Tyr Leu Val Ser Asn Leu Glu Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Leu Gln Ala
                85                  90                  95

Thr His Phe Pro Leu Thr Phe Gly Ala Gly Ala Lys Leu Glu Leu Lys
                100                 105                 110

<210> SEQ ID NO 32
<211> LENGTH: 112
<212> TYPE: PRT
<213> ORGANISM: Artificial Sequence
<220> FEATURE:
<223> OTHER INFORMATION: light chain variable region

<400> SEQUENCE: 32

```
Asp Ile Val Leu Thr Gln Ser Pro Leu Phe Leu His Val Ser Leu Gly
1               5                   10                  15

Asp Gln Ala Ser Ile Ser Cys Thr Ser Ser Gln Ser Leu Val His Ser
                20              25                  30

Asn Gly Asn Ser Tyr Leu Asp Trp His Leu Gln Lys Ser Asp Gln Ser
            35              40                  45

Leu Gln Leu Leu Ile Tyr Glu Val Ser Lys Arg Asn Ser Gly Val Pro
    50              55              60

Asp Arg Phe Ser Gly Ser Gly Ser Gly Lys Asp Phe Thr Leu Lys Ile
65              70              75                      80

Ser Arg Val Glu Pro Glu Asp Leu Gly Ile Tyr Tyr Cys Phe Gln Arg
                85              90                  95

Thr His Leu Pro Leu Thr Phe Gly Ala Gly Thr Lys Leu Glu Ile Lys
            100             105             110
```